US011819435B2

(12) United States Patent
Ong et al.

(10) Patent No.: US 11,819,435 B2
(45) Date of Patent: Nov. 21, 2023

(54) DEVICE FOR PROVIDING ACTIVE ASSISTANCE TO A BODY JOINT

(71) Applicant: Delsson Singapore Pte Ltd, Singapore (SG)

(72) Inventors: Fabian Eng Ann Ong, Singapore (SG); Christopher Khim Yam Lim, Singapore (SG); Philip Kwok Nan Loh, Singapore (SG)

(73) Assignee: Delsson Singapore Pte Ltd, Singapore (SG)

(*) Notice: Subject to any disclaimer, the term of this patent is extended or adjusted under 35 U.S.C. 154(b) by 164 days.

(21) Appl. No.: 17/208,586

(22) Filed: Mar. 22, 2021

(65) Prior Publication Data
US 2021/0290420 A1    Sep. 23, 2021

(30) Foreign Application Priority Data

Mar. 23, 2020    (SG) ............................ 10202002663R

(51) Int. Cl.
*A61F 5/01*    (2006.01)
(52) U.S. Cl.
CPC ............ *A61F 5/0125* (2013.01); *A61F 5/013* (2013.01); *A61F 2005/0179* (2013.01)
(58) Field of Classification Search
CPC .............. A61F 13/08; A61F 2007/0043; A61F 5/0109; A61F 2013/00093; A61F 5/0111;
(Continued)

(56) References Cited

U.S. PATENT DOCUMENTS 5,129,898 A * 7/1992 Brusasco ............... A61B 17/66
                                                    606/56
5,352,190 A * 10/1994 Fischer ................. A61H 1/024
                                                    602/26
(Continued)

FOREIGN PATENT DOCUMENTS

EP    0941722 A1 * 3/1999 ........... A61F 5/0123
FR    2552660 A1    4/1985
(Continued)

OTHER PUBLICATIONS

Gunter Zaltenbach, "Knee support device, especially for skiers", Nov. 1987, All pages (Year: 1987).*

(Continued)

*Primary Examiner* — Alireza Nia
*Assistant Examiner* — Eric Richard McQuiggan

(57) ABSTRACT

A device for providing active assistance to a body joint including at least one spring module interconnecting first and second attachment parts. The at least one spring module including first and second elongate link members coupled to the first and second attachment parts respectively and pivotably coupled to each other at a pivot joint with a pivoting axis perpendicular to the first and second elongate link members; a coil spring extending longitudinally between the first and second elongate link members and across the pivot joint, whereby first and second ends of the coil spring are coupled to the first and second elongate link members respectively; and a coil-spring-retaining-member slidable relative to the first elongate link member in a manner so as to vary a portion of a length of the coil spring engaged and retained by the coil-spring-retaining-member to vary an effective length of the coil spring.

16 Claims, 15 Drawing Sheets

(58) Field of Classification Search
CPC ...... A61F 5/0123; A61F 5/0125; A61F 5/013; A61F 5/00; A61F 5/0102; A61F 5/0585; A61F 2005/0132; A61F 5/0106; A61F 13/061; A61F 2005/0197; A61F 5/0118; A61F 5/04; A61F 5/048; A61F 2005/0137–0188; D04B 1/265; D04B 1/26; A41B 11/003; A63B 21/023; A63B 21/4047; A63B 21/00069; A61H 1/0237; A61H 1/024

See application file for complete search history.

(56) References Cited

U.S. PATENT DOCUMENTS

| | | | | |
|---|---|---|---|---|
| 5,653,680 | A * | 8/1997 | Cruz | A61F 5/013 482/45 |
| 6,171,272 | B1 * | 1/2001 | Akita | A61F 5/0127 602/27 |
| 6,245,034 | B1 * | 6/2001 | Bennett | A61F 5/0125 602/20 |
| 8,882,688 | B1 * | 11/2014 | Ancinec | A61F 5/0125 128/882 |
| 2005/0059916 | A2 * | 3/2005 | Enzerink | A61F 5/0125 602/26 |
| 2015/0119777 | A1 | 4/2015 | Garrish | |
| 2016/0361222 | A1 * | 12/2016 | Publicover | A61F 5/0123 |
| 2018/0098864 | A1 | 4/2018 | Auberger et al. | |

FOREIGN PATENT DOCUMENTS

| | | | | |
|---|---|---|---|---|
| KR | | 101455330 B1 * | 8/2013 | ............. A61F 2/644 |
| WO | WO1987006820 A1 * | | 5/1987 | ........... A61F 5/0125 |

OTHER PUBLICATIONS

이상현 (Lee), "Joint activity aids for the human body", Oct. 2014, All pages (Year: 2014).*

Levitation Knee Brace—Spring Loaded Technology, https://springloadedtechnology.com/product/levitation-knee-brace/ 7 pages.

Search Report completed Sep. 15, 2020 from Intellectual Property Office of Singapore, Application No. 10202002663R filed Mar. 23, 2020, 2 pages.

Written Opinion completed Oct. 26, 2020 from Intellectual Property Office of Singapore, Application No. 10202002663R filed Mar. 23, 2020, 5 pages.

* cited by examiner

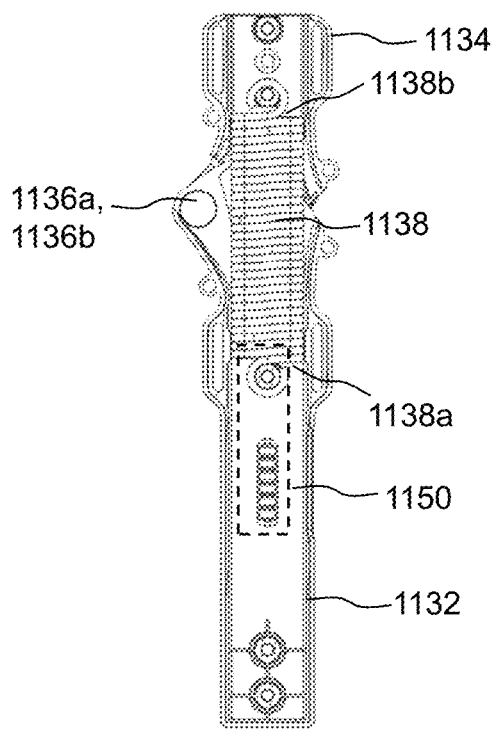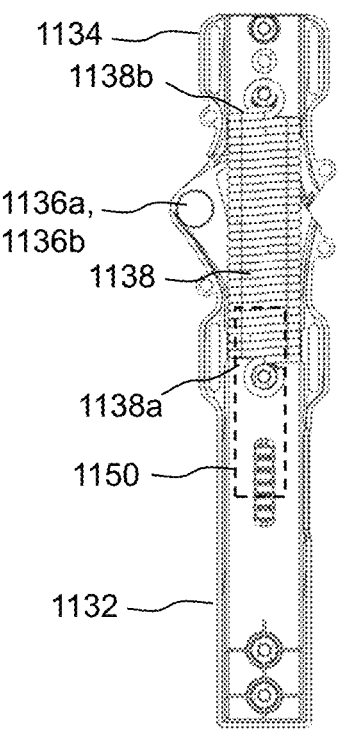
FIG. 12A  FIG. 12B
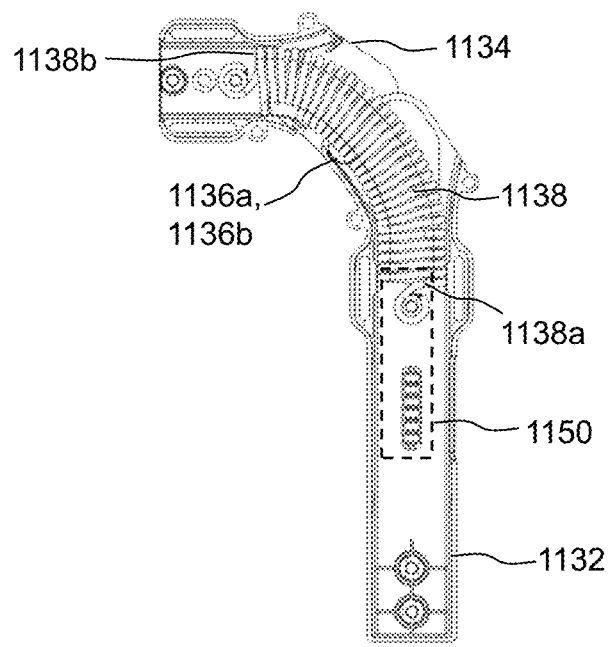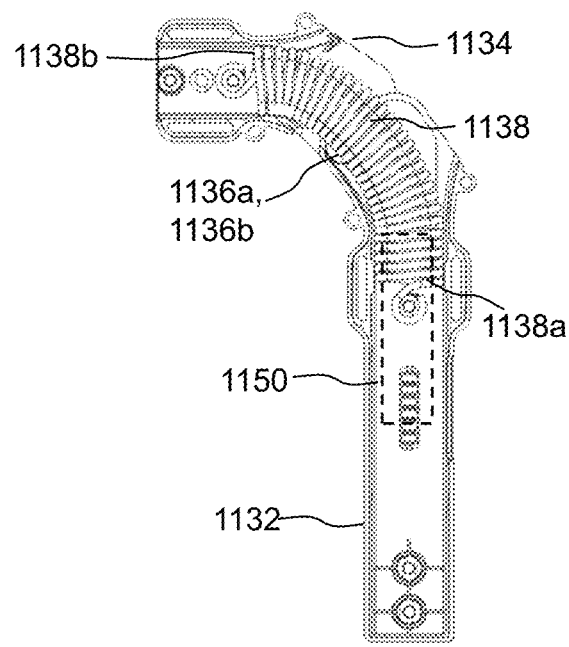
FIG. 13A  FIG. 13B

DEVICE FOR PROVIDING ACTIVE ASSISTANCE TO A BODY JOINT

CROSS REFERENCE TO RELATED APPLICATIONS

The present application claims the benefit of Singapore patent application no. 10202002663R filed on 23 Mar. 2020, the entire contents of which are incorporated herein by reference for all purposes.

TECHNICAL FIELD

Various embodiments generally relate to a device for providing active assistance to a body joint between a first portion and a second portion of a body.

BACKGROUND

An orthosis or a brace is generally an externally applied device serving to support a body joint or to prevent or assist relative movement of the body joint. Typically, the orthosis or the brace is configured to provide passive support or assistance by controlling, guiding, limiting and/or immobilizing the body joint. For example, prophylactic knee braces, functional knee braces, and rehabilitation knee braces are common orthosis providing passive support to the knee. In recent years, orthoses or braces which provide active assistance to relief stress at the body joint during movements have been developed. These orthoses or braces are configured to provide an assistive force to augment a movement of the body joint. However, in order to provide sufficient assistive force for meaningful augmentation of the movement of the body joint, complicated assistive force mechanism or system with multiple parts and uncommon components have been incorporated. These assistive force mechanism or system generally requires extensive manufacturing support for the multiple parts, special fabrication procedures for the uncommon components and complex installation procedures leading to high costs.

Accordingly, there is a need for a simpler and effective device for providing active assistance to a body joint so as to address the above issues.

SUMMARY

According to various embodiments, there is provided a device for providing active assistance to a body joint between a first portion and a second portion of a body. The device may include a first attachment part configured to hold the device to the first portion of the body, a second attachment part configured to hold the device to the second portion of the body, and at least one spring module interconnecting the first attachment part and the second attachment part. The at least one spring module may include a first elongate link member coupled to the first attachment part. The at least one spring module may include a second elongate link member coupled to the second attachment part. The first elongate link member and the second elongate link member may be pivotably coupled to each other at a pivot joint with a pivoting axis perpendicular to the first and second elongate link members. The at least one spring module may include a coil spring extending longitudinally between the first and second elongate link members and across the pivot joint. A first end of the coil spring may be coupled to the first elongate link member and a second end of the coil spring may be coupled to the second elongate link member. The at least one spring module may further include a slidable coil-spring-retaining-member at the first elongate link member. The coil-spring-retaining-member may be slidable relative to the first elongate link member in a manner so as to vary a portion of a length of the coil spring, from the first end of the coil spring towards the second end, engaged and retained by the coil-spring-retaining-member to vary an effective length of the coil spring.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which:

FIG. 12A and FIG. 12B show longitudinal cross-sectional views of the spring module of FIG. 11A in the longitudinally aligned disposition according to various embodiments;

FIG. 13A and FIG. 13B show cross-sectional views of the spring module of FIG. 11A with first and second elongate link members pivoted relative to each other according to various embodiments.

DETAILED DESCRIPTION

Figure 1A:
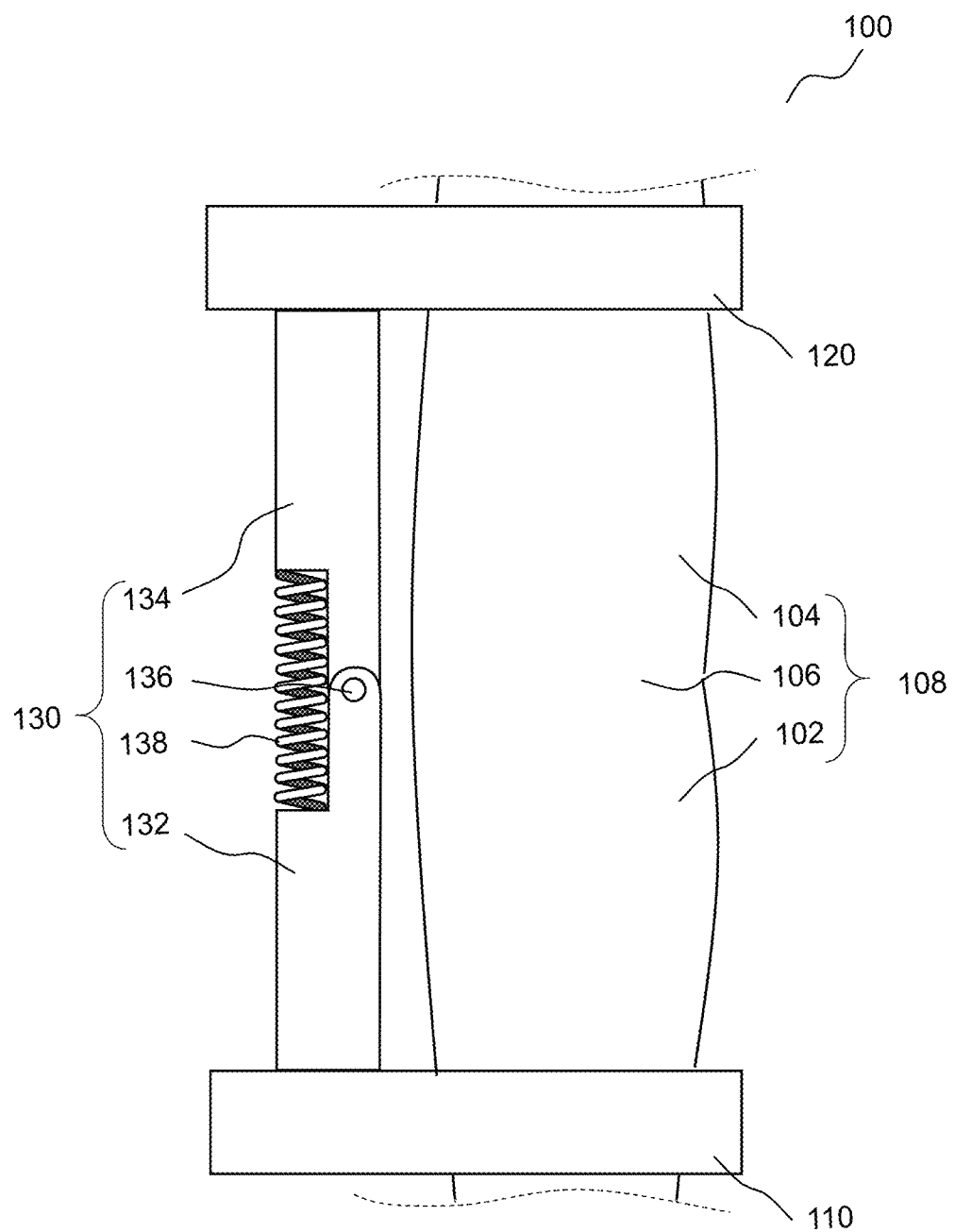
FIG. 1A and FIG. 1B show schematic diagrams of a device for providing active assistance to a body joint between a first portion and a second portion of a body according to various embodiments.

Embodiments described below in the context of the apparatus are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "lateral", "side", "up", "down" etc., when used in the following description are used for convenience and to aid understanding of relative positions or directions, and not intended to limit the orientation of any device, or structure or any part of any device or structure. In addition, the singular terms "a", "an", and "the" include plural references unless context clearly indicates otherwise. Similarly, the word "or" is intended to include "and" unless the context clearly indicates otherwise.

Various embodiments generally relate to a device for providing active assistance to a body joint between a first portion and a second portion of a body. According to various embodiments, the device may include an orthosis or a brace configured to provide active assistance to the body joint. According to various embodiments, the body joint may include, but not limited to, an ankle, a knee, an elbow, a wrist, a neck, a shoulder, a waist, or a pelvic, etc. According to various embodiments, the device may be configured to provide an assistive force to augment a movement of the body joint. According to various embodiments, the device may include a spring module configured to provide a resistive force against a first relative movement between the first portion and the second portion of the body in a first direction so as to prevent hyperextension of the joint while the spring module is being loaded by the first relative movement, and to provide an assistive force to augment a second relative movement between the first portion and the second portion of the body in a second direction, which is opposite the first direction, so as to relief stress at the body joint as the spring module is being unloaded by the second relative movement. According to various embodiments, the device may be used in various stages of recovery from an injury of the body joint. According to various embodiments, the device may function as a tool for physiotherapist to train or retrain their patients for faster recovery of the body joint.

Various embodiments seek to provide a modular and adaptive device for providing active assistance to the body joint between the first portion and the second portion of the body. According to various embodiments, the spring module of the device may be configured to be modular such that the spring module may be easily installed, removed, and replaced. According to various embodiments, the spring module of the device may be configured to be customizable for allowing adjustment of the resistance so as to vary the assistance provided by the device to the user for different activities. For examples, from sitting to standing position, climbing stairs, lifting weights etc. Accordingly, the spring module may allow the user to vary or customize the resistance to carry more load or to give more assistance to the user. According to various embodiments, the spring module of the device may be adaptable to users of different body weight and size.

According to various embodiments, the device may be light weight and may be configured to comfortably fit to the body joint, the first portion and the second portion of the body. According to various embodiments, the spring module may be of a simple configuration with few parts and simple mechanism, thus contributing to the light weight of the device as well as sleek configuration for a comfortable fit.

According to various embodiments, the spring module of the device may include a coil spring arranged and applied, in a unique manner which is also easy and simple to install, so to provide the resistive force against the first relative movement between the first portion and the second portion of the body in the first direction and the assistive force to augment the second relative movement between the first portion and the second portion of the body in the second direction. Conventionally, the use of coil spring has been avoided in orthoses or braces which provide active assistance because (i) coil spring generally cannot produce the force required, for example to assist a person from a sitting to a standing position, when used in the traditional way of compression or extension, (ii) a very large coil spring would be required to provide the force would render the device too bulky, and (iii) the very large coil spring would also be heavy which would add to the weight of the device rendering the device not user friendly. Thus, the unique arrangement and application of the coil spring in the spring module of the device according to the various embodiments is not only distinct and different from the existing orthoses or braces which provide active assistance, it also goes against the generally accepted view and practices whereby the use of coil spring is avoided in such orthoses or braces. According to various embodiments, the coil spring of the spring module is arranged and applied such that the coil spring bends about the body joint, instead of the conventional way of compression or extension, when the first portion and the second portion of the body move relative to each other.

According to various embodiments, when the device is a knee orthosis or a knee brace, the spring module of the device may be configured to produce a force of no less than 30% of the user average body weight to be sufficient to help the user with knee injury to move from a sitting to a standing position without assistance from another person. According to various embodiments, the spring module of the device may be configured to produce a force sufficient to satisfy the "one Knee Test", whereby the user in a sitting position straightens one leg until it is parallel to the ground and uses the other leg to lift himself off the chair to a standing position without any other external aid or assistance.

According to various embodiments, the device may be configured to be light and comfortable such that the user would be able to use the device for extended duration without discomfort while the device assist the user in activities requiring movement of the injured body joint that would not be possible without the assistance of the device. According to various embodiments, the device may be configured to be easy to manufacture and simple to use.

According to various embodiments, the device may be configured to be modular, small, light and yet powerful enough to assist movement of the body joint which may be weaken due to injury or recovering from surgery. According to various embodiments, the device may be configured to be upgradable and customizable to adapt to the various stages of recovery of each individual because everyone recovers at a different rate. According to various embodiments, being modular enables the adjustment of the strength of the coil spring to accommodate various stages of recovery without having to change the entire device because the spring and/or the spring module may be a modular component. Accordingly, a very large profile of forces may be available for the user.

According to various embodiments, the device may be configured to assist the user with injury to the body joint or recovering from surgery or with weakness in the joint, without the need for assistance from another person, by reducing stress on the body joint. According to various embodiments, the device may provide the user a sense of psychological independence and freedom which may be important. According to various embodiments, the device may not replace the need for the user to use his/her own muscles, but may assist recovery by providing a customizable resistance.

According to various embodiments, the coil spring of the spring module of the device may be configured to provide a force to replace or enhance the action of the muscles and ligaments associated with the body joint to which the device is attached.

The following examples pertain to various embodiments.

Example 1 is a device for providing active assistance to a body joint between a first portion and a second portion of a body, the device including:
- a first attachment part configured to hold the device to the first portion of the body;
- a second attachment part configured to hold the device to the second portion of the body; and
- at least one spring module interconnecting the first attachment part and the second attachment part, the at least one spring module includes
  - a first elongate link member coupled to the first attachment part;
  - a second elongate link member coupled to the second attachment part, wherein the first elongate link member and the second elongate link member are pivotably coupled to each other at a pivot joint with a pivoting axis perpendicular to the first and second elongate link members; and
  - a coil spring extending longitudinally between the first and second elongate link members and across the pivot joint, wherein a first end of the coil spring is coupled to the first elongate link member and a second end of the coil spring is coupled to the second elongate link member,
  - wherein the at least one spring module further comprises a slidable coil-spring-retaining-member at the first elongate link member, the coil-spring-retaining-member being slidable relative to the first elongate link member in a manner so as to vary a portion of a length of the coil spring, from the first end of the coil spring towards the second end, engaged and retained by the coil-spring-retaining-member to vary an effective length of the coil spring.

In Example 2, the subject matter of Example 1 may optionally include that the coil spring of the at least one spring module may be configured to provide a torque, based on a lateral stiffness of the coil spring, against a relative pivoting motion about the pivot joint between the first and second elongate link members from a longitudinally aligned disposition of the first and second elongate link members.

In Example 3, the subject matter of Example 1 or 2, may optionally include that the coil spring may include rectangular-shaped coil spring, pill-shaped coil spring, or wedged-shape coil spring.

In Example 4, the subject matter of any one of Examples 1 to 3 may optionally include that the coil-spring-retaining-member may include a coil-spring-retaining-insert slidable relative to the first elongate link member in a manner so as to vary a length of the coil-spring-retaining-insert, from a free end of the coil-spring-retaining-insert towards an opposite end, slidably inserted within the coil spring from the first end thereof to vary the portion of the length of the coil spring engaged and retained by the coil-spring-retaining-insert to vary the effective length of the coil spring.

In Example 5, the subject matter of any one of Examples 1 to 3 may optionally include that the coil-spring-retaining-member may include a coil-spring-retaining-bracket slidable relative to the first elongate link member in a manner so as to vary the length of the coil spring, from the first end of the coil spring towards the second end, engaged and retained within the coil-spring-retaining-bracket to vary the effective length of the coil spring.

In Example 6, the subject matter of any one of Examples 1 to 5 may optionally include that the at least one spring module may further include a locking mechanism to lock the slidable coil-spring-retaining-member to the first elongate link member.

In Example 7, the subject matter of any one of Examples 1 to 6 may optionally include that a longitudinal end portion of the first elongate link member may include a diagonal arm extending therefrom, a longitudinal end portion of the second elongate link member may include a diagonal arm extending therefrom, and a tip portion of the diagonal arm of the first elongate link member may be pivotably coupled to a tip portion of the diagonal arm of the second elongate link member in a manner so as to form the pivot joint immediately adjacent a mid-segment of the coil spring when the coil spring is aligned with the first and second elongate link members.

In Example 8, the subject matter of any one of Examples 1 to 7 may optionally include that the first elongate link member may include a hollow frame wherein the first end of the coil spring is inserted into the first elongate link member and coupled to an inner wall surface of the first elongate link member, and the second elongate link member may include a hollow frame wherein the second end of the coil spring is inserted into the second elongate link member and coupled to an inner wall surface of the second elongate link member.

In Example 9, the subject matter of Example 8 in combination with Example 4 may optionally include that the coil-spring-retaining-insert may be slidable inside the hollow frame of the first elongate link member, the first elongate link member may include a longitudinal slot along a wall portion of the hollow frame, and the coil-spring-retaining-insert may include a protrusion extending from the coil-spring-retaining-insert and through the longitudinal slot.

In Example 10, the subject matter of any one of Examples 1 to 9 may optionally include that each of the first attachment part and the second attachment part may include a curved-bracket having a curvature extending from a first end to a second end, the curvature of the curved-bracket being shaped to correspond to a transverse contour of the first portion and the second portion of the body respectively.

In Example 11, the subject matter of Example 10 may optionally include that the at least one spring module may interconnect the first end of the curved-bracket of the first attachment part and the first end of the curved-bracket of the second attachment part, the first elongate link member may be coupled directly to the first end of the curved-bracket of the first attachment part, the second elongate link member may be coupled directly to the first end of the curved-bracket of the second attachment part, and the device may be free of other components interconnecting the first end of the curved-bracket of the first attachment part and the first end of the curved-bracket of the second attachment part.

In Example 12, the subject matter of Example 10 or 11 may optionally include a linkage assembly interconnecting the second end of the curved-bracket of the first attachment part and the second end of the curved-bracket of the second attachment part, the linkage assembly includes a first link rod coupled to the second end of the curved-bracket of the first attachment part; and a second link rod coupled to the second end of the curved-bracket of the second attachment part, wherein the first link rod and the second link rod are pivotably coupled to each other at a pivot joint which is coaxial with the pivot joint between the first and second elongate link members of the at least one spring module.

In Example 13, the subject matter of Example 10 or 11 may optionally include that the device may include a first spring module interconnecting the first end of the curved-bracket of the first attachment part and the first end of the curved-bracket of the second attachment part, and a second spring module interconnecting the second end of the curved-bracket of the first attachment part and the second end of the curved-bracket of the second attachment part.

In Example 14, the subject matter of Example 13 may optionally include that the device may be free of other components interconnecting the first attachment part and the second attachment part.

In Example 15, the subject matter of any one of Examples 1 to 14 may optionally include that the at least one spring module may be removably coupled to the first attachment part and the second attachment part.

In Example 16, the subject matter of any one of Examples 1 to 6, 10 to 15 may optionally include that the first elongate link member and the second elongate link member may be pivotably coupled to each other via a pair of coaxial pivot joints with a common pivoting axis perpendicular to the first and second elongate link members.

In Example 17, the subject matter of Example 16 may optionally include that the at least one spring module may bend with a mid-segment of the coil spring slides between the pair of coaxial pivot joints in a manner so as to intersect the common pivoting axis when the first elongate link member and the second elongate link member are pivoted relative to each other about the common pivoting axis to form an angle with respect to each other.

In Example 18, the subject matter of Example 16 or 17 may optionally include that the first elongate link member may include a hollow frame, wherein the first end of the coil spring may be inserted into the first elongate link member and coupled to an inner wall surface of the first elongate link member, and the second elongate link member may include a hollow frame, wherein the second end of the coil spring may be inserted into the second elongate link member and coupled to an inner wall surface of the second elongate link member.

In Example 19, the subject matter of Example 18 may optionally include that the first elongate link member may include a first hole and a second hole at an longitudinal end portion thereof, and the second elongate link member may include a first hole and a second hole at an longitudinal end portion thereof, wherein the first hole of the first elongate link member may be coupled to the first hole of the second elongate link member via a first pin to form a first pivot joint of the pair of coaxial pivot joints and the second hole of the first elongate link member may be coupled to the second hole of the second elongate link member via a second pin to form a second pivot joint of the pair of coaxial pivot joints.

In Example 20, the subject matter of Example 19 may optionally include that the first elongate link member may include a bending support extending diagonally at the longitudinal end portion of the first elongate link member for propping or holding up the mid-segment of the coil spring to bend the coil spring when the first elongate link member and the second elongate link members pivot about the common pivoting axis.

Figure 1B:
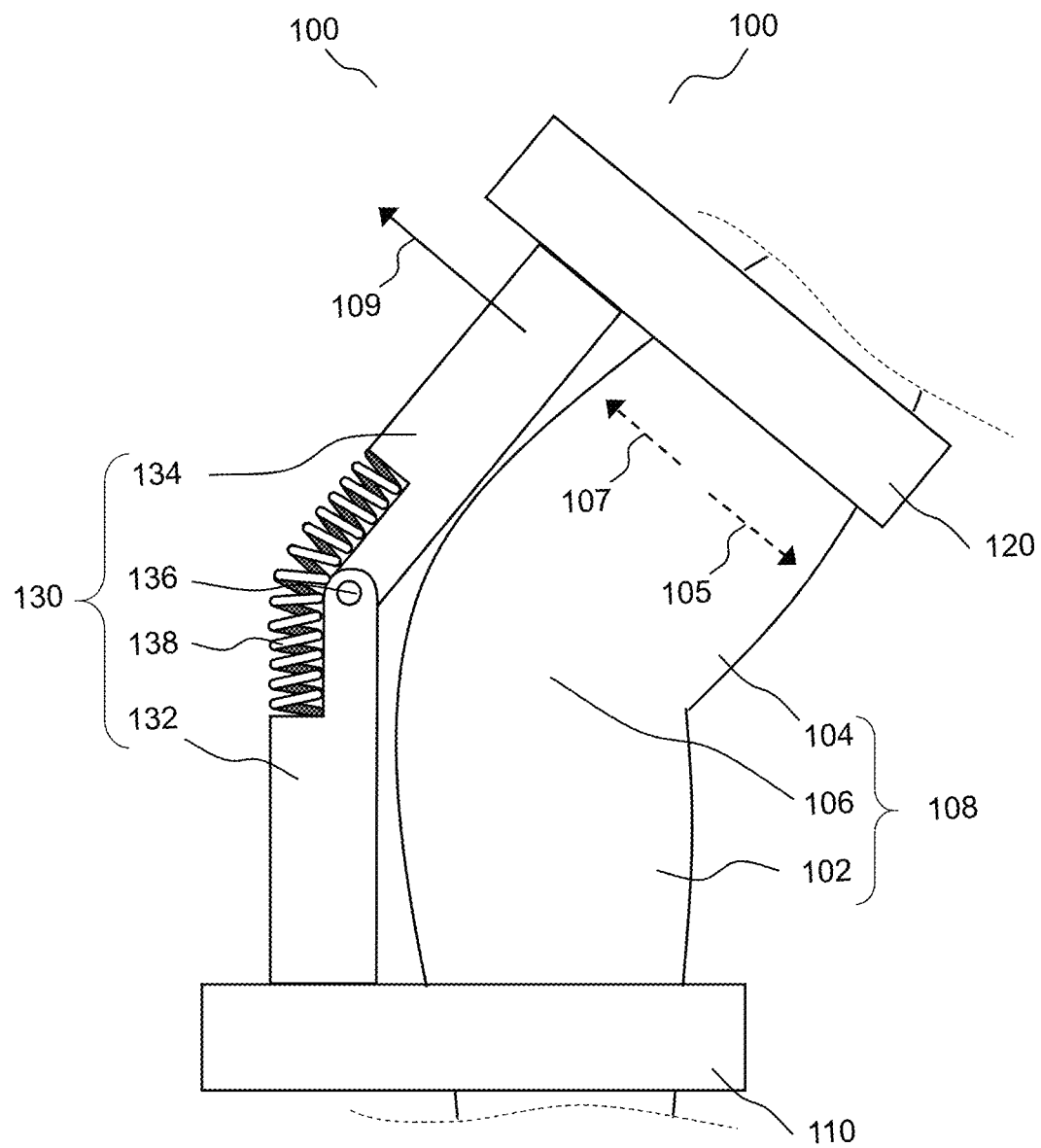

FIG. 1A and FIG. 1B show schematic diagrams of a device 100 for providing active assistance to a body joint 106 between a first portion 102 and a second portion 104 of a body 108 according to various embodiments. FIG. 1A shows the device 100 in a neutral position whereby the body 108 is relaxed and the stress at the body joint 106 is minimum. FIG. 1B shows the device 100 providing an active force which acts against a bending motion of the body 108 about the body joint 106 and augments a straightening motion of the body 108 about the body joint 106. According to various embodiments, the device 100 may be an orthosis or a brace which is applied externally to the first portion 102 and the second portion 104 of a body 108 so as to support the body joint 106 or to prevent or assist relative movement of the body joint 106. According to various embodiments, the first portion 102 of the body 108 may be on one side of the body joint 106 and the second portion 104 of the body 108 may be on an opposite side of the body joint 106 such that bending or straightening of the body 108 may result in a corresponding relative pivoting motion between the first portion 102 and the second portion 104 of a body 108 about the body joint 106. According to various embodiments, the body joint 106 may include, but not limited to, an ankle, a knee, an elbow, a wrist, a neck, a shoulder, a waist, or a pelvic, etc.

According to various embodiments, the device 100 may be configured to provide the force 109 to resist against a first relative pivot motion between the first portion 102 and the second portion 104 of the body 108 about the body joint 106 in a first direction 105 during bending of the body 108 so as to prevent hyperextension of the body joint 106. According to various embodiments, the same force 109 may augment a second relative pivot motion between the first portion 102 and the second portion 104 of the body 108 about the body joint 106 in a second direction 107, which is opposite the first direction 105, during straightening of the body 108 so as to relief stress at the body joint 106.

According to various embodiments, the device 100 may include a first attachment part 110 configured to hold the device 100 to the first portion 102 of the body 108. According to various embodiments, the first attachment part 110 may include any suitable securing arrangement to hold the device 100 to the first portion 102 of the body 108. For example, the first attachment part 110 may include any one or a combination of: a rigid securing arrangement such as a hinged clamp, a hinged rigid cuff, a hinged bracket, etc.; or a flexible securing arrangement such as a band, a strap, a flexible cuff, a belt, a strip, a Velcro, a sock, a bandage, a wrap, a sleeve, etc.; or a combined rigid and flexible securing arrangement having a rigid element, such as a clamp or a rigid cuff or a bracket or a jaw or a shell, and a flexible element, such as a band or a strap or a flexible cuff or a belt or a strip or a Velcro or a sock or a bandage or a wrap or a sleeve, forming a single securing unit.

According to various embodiments, the device 100 may include a second attachment part 120 configured to hold the device 100 to the second portion 104 of the body 108. According to various embodiments, the second attachment part 120 may include any suitable securing arrangement to hold the device 100 to the second portion 104 of the body 108. For example, the second attachment part 120 may include any one or a combination of: a rigid securing arrangement such as a hinged clamp, a hinged rigid cuff, a hinged bracket, etc.; or a flexible securing arrangement such as a band, a strap, a flexible cuff, a belt, a strip, a Velcro, a sock, a bandage, a wrap, a sleeve, etc.; or a combined rigid and flexible securing arrangement having a rigid element, such as half a clamp or half a rigid cuff or half a bracket, and a flexible element, such as a band or a strap or a flexible cuff or a belt or a strip or a Velcro or a sock or a bandage or a wrap or a sleeve, forming a single securing unit.

According to various embodiments, the device 100 may include at least one spring module 130 interconnecting the first attachment part 110 and the second attachment part 120. Accordingly, the at least one spring module 130 may be extending between the first attachment part 110 and the second attachment part 120, and connecting the first attachment part 110 and the second attachment part 120 together. Hence, the first attachment part 110 may be connected to the second attachment part 120 via the at least one spring module 130.

According to various embodiments, the at least one spring module 130 of the device 100 may include a first elongate link member 132 coupled to the first attachment part 110. Accordingly, the first elongate link member 132 may be fastened or secured or connected or joined to the first attachment part 110 in a manner so as to prevent relative movement or rotation between the first elongate link member 132 and the first attachment part 110. According to various embodiments, the first elongate link member 132 may be coupled to the first attachment part 110 in a manner such that the first elongate link member 132 may also be detachable from the first attachment part 110. Accordingly, the first elongate link member 132 and the first attachment part 110 may be configured to be capable of being coupled together and also capable of being detached from each other. Hence, the first elongate link member 132 may be removably coupled to the first attachment part 110. According to various embodiments, the first elongate link member 132 may be coupled to the first attachment part 110 via, screw, bolt and nut, clamp, clip, latch, hook, pin, or any other suitable fastener.

According to various embodiments, the at least one spring module 130 of the device 100 may include a second elongate link member 134 coupled to the second attachment part 120. Accordingly, the second elongate link member 134 may be fastened or secured or connected or joined to the second attachment part 120 in a manner so as to prevent relative movement or rotation between the second elongate link member 134 and the second attachment part 120. According to various embodiments, the second elongate link member 134 may be coupled to the second attachment part 120 in a manner such that the second elongate link member 134 may also be detachable from the second attachment part 120. Accordingly, the second elongate link member 134 and the second attachment part 120 may be configured to be capable of being coupled together and also capable of being detached from each other. Hence, the second elongate link member 134 may be removably coupled to the second attachment part 120.

According to various embodiments, the second elongate link member 134 may be coupled to the second attachment part 120 via, screw, bolt and nut, clamp, clip, latch, hook, pin, or any other suitable fastener.

According to various embodiments, the first elongate link member 132 and the second elongate link member 134 may be pivotably coupled to each other at a pivot joint 136 with a pivoting axis perpendicular to the first and second elongate link members 132, 134. According to various embodiments, the first elongate link member 132 and the second elongate link member 134 may be pivotable relative to each other about the pivot joint 136 such that the first elongate link member 132 and the second elongate link member 134 may be moved relative to each other so as to form an angle with respect to each other at the pivot joint 136.

According to various embodiments, the at least one spring module 130 may include a coil spring 138 extending longitudinally between the first and second elongate link members 132, 134 and across the pivot joint 136. Accordingly, the coil spring 138 may extend across the pivoting axis of the pivot joint 136 so as to form a cross configuration with the pivoting axis of the pivot joint 136. According to various embodiments, the coil spring 138 may extend across the pivot joint 136 in a manner so as to be over the pivot joint 136, or under the pivot joint 136, or intersecting the pivoting axis of the pivot joint 136. According to various embodiments, the coil spring 138 may intersect the pivoting axis of the pivot joint 136 when the coil spring 138 extends across an end of the pivot joint 136 in a manner so as to be abutting or adjacent to the end of the pivot joint 136. As shown in FIG. 1A and FIG. 1B, the coil spring 138 may extend across and over the pivot joint 136. According to various embodiments, a first end 138a of the coil spring 138 may be coupled to the first elongate link member 132 and a second end 138b of the coil spring 138 may be coupled to the second elongate link member 134. According to various embodiments, the coil spring 138 may be arranged and disposed with respect to the first and second elongate link member 132, 134 in a manner such that a longitudinal axis of the coil spring 138 may extend from the first elongate link member 132 to the second elongate link member 134, whereby a first end segment of the coil spring 138 towards the first end 138a may be parallel to the first elongate link member 132 and a second end segment of the coil spring 138 towards the second end 138b may be parallel to the second elongate link member 134. According to various embodiments, a direction of a length of the coil spring 138 may be extending between the first and second elongate link members 132, 134 such that the coil spring 138 runs lengthwise from the first elongate link member 132 to the second elongate link member 134. According to various embodiments, the coil spring 138 may extend or run between the first and second elongate link members 132, 134 with the first end segment of the coil spring 138 running alongside at least a portion of a length of the first elongate link member 132, a mid-segment of the coil spring 138 running across the pivot joint 136 (e.g. over the pivot joint 136 as shown), and a second end segment of the coil spring 138 running alongside at least a portion of a length of the second elongate link member 134. According to various embodiments, when the first elongate link member 132 and the second elongate link member 134 forms an angle of 180° with respect to each other at the pivot joint 136, the coil spring 138 may be parallel to the first and second elongate link member 132, 134. Accordingly, the coil spring 138 may be aligned to the first and second elongate link member 132, 134 such that the first end segment of the coil spring 138 may be overlapping or side-by-side or alongside or coincide with at least a portion of a length of the first elongate link member 132, the second end segment of the coil spring 138 may be overlapping or side-by-side or alongside or coincide with at least a portion of a length of the second elongate link member 134, and the mid-segment of the coil spring 138 may lie across the pivot joint 136.

According to various embodiments, the first end 138a of the coil spring 138 may be fastened or secured or connected or joined to the first elongate link member 132 in a manner such that the first end 138a of the coil spring 138 may remain stationary or may not be movable relative to the first elongate link member 132. According to various embodiments, the first end 138a of the coil spring 138 may be coupled to the first elongate link member 132 in a manner such that the first end 138a of the coil spring 138 may also be detachable from the first elongate link member 132. Accordingly, the first end 138a of the coil spring 138 and the first elongate link member 132 may be configured to be capable of being coupled together and also capable of being detached from each other. Hence, the first end 138a of the coil spring 138 may be removably coupled to the first elongate link member 132.

According to various embodiments, the second end 138b of the coil spring 138 may be fastened or secured or connected or joined to the second elongate link member 134 in a manner such that the second end 138b of the coil spring 138 may remain stationary or may not be movable relative to the second elongate link member 134. According to various embodiments, the second end 138b of the coil spring 138 may be coupled to the second elongate link member 134 in a manner such that the second end 138b of the coil spring 138 may also be detachable from the second elongate link member 134. Accordingly, the second end 138b of the coil spring 138 and the second elongate link member 134 may be configured to be capable of being coupled together and also capable of being detached from each other. Hence, the second end 138b of the coil spring 138 may be removably coupled to the second elongate link member 134.

According to various embodiments, with the first elongate link member 132 removably coupled to the first attachment part 110 and the second elongate link member 134 removably coupled to the second attachment part 120, the at least one spring module 130 may be modular with respect to the device 100 and may be easily replaceable with another spring module. Accordingly, the at least one spring module 130 may be removably coupled to the first attachment part 110 and the second attachment part 120. According to various embodiments, with the first end 138a of the coil spring 138 removably coupled to the first elongate link member 132 and the second end 138b of the coil spring 138 may be removably coupled to the second elongate link member 134, the coil spring 138 may be modular with respect to the at least one spring module 130 and may be easily replaceable with another coil spring.

Accordingly, the coil spring 138 may be removably coupled to the first and second elongate link members 132, 134 of the at least one spring module 130.

According to various embodiments, with the coil spring 138 arranged and applied in the at least one spring module 130 which interconnects the first attachment part 110 secured to the first portion 102 of the body 108 and the second attachment part 120 secured to the second portion 104 of the body, the coil spring 138 may provide a torque or a force, based on a lateral stiffness of the coil spring 138, against a first relative pivoting motion about the pivot joint 136 between the first and second elongate link members 132, 134 from a longitudinally aligned disposition of the first and second elongate link members 132, 134 during a bending motion of the first and second portions 102, 104 of the body 108. The same torque or force provided by the coil spring 138, based on the lateral stiffness of the coil spring 138, may also augment a second relative pivoting motion about the pivot joint 136 between the first and second elongate link members 132, 134 to return to the longitudinally aligned disposition of the first and second elongate link members 132, 134 during a straightening motion of the first and second portions 102, 104 of the body 108.

Figure 2A:
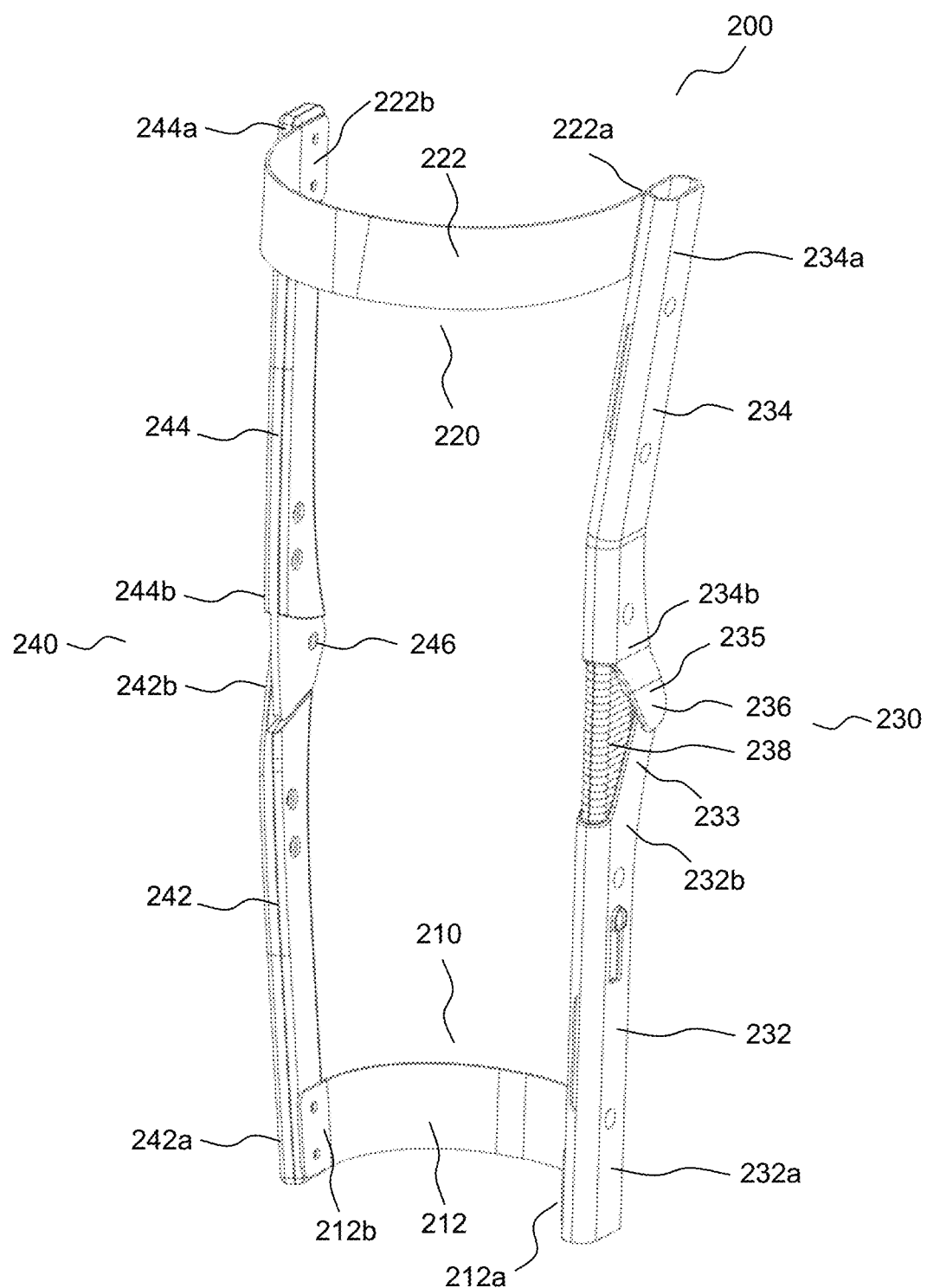
FIG. 2A and FIG. 2B show a device for providing active assistance to a body joint between a first portion and a second portion of a body according to various embodiments.
Figure 2B:
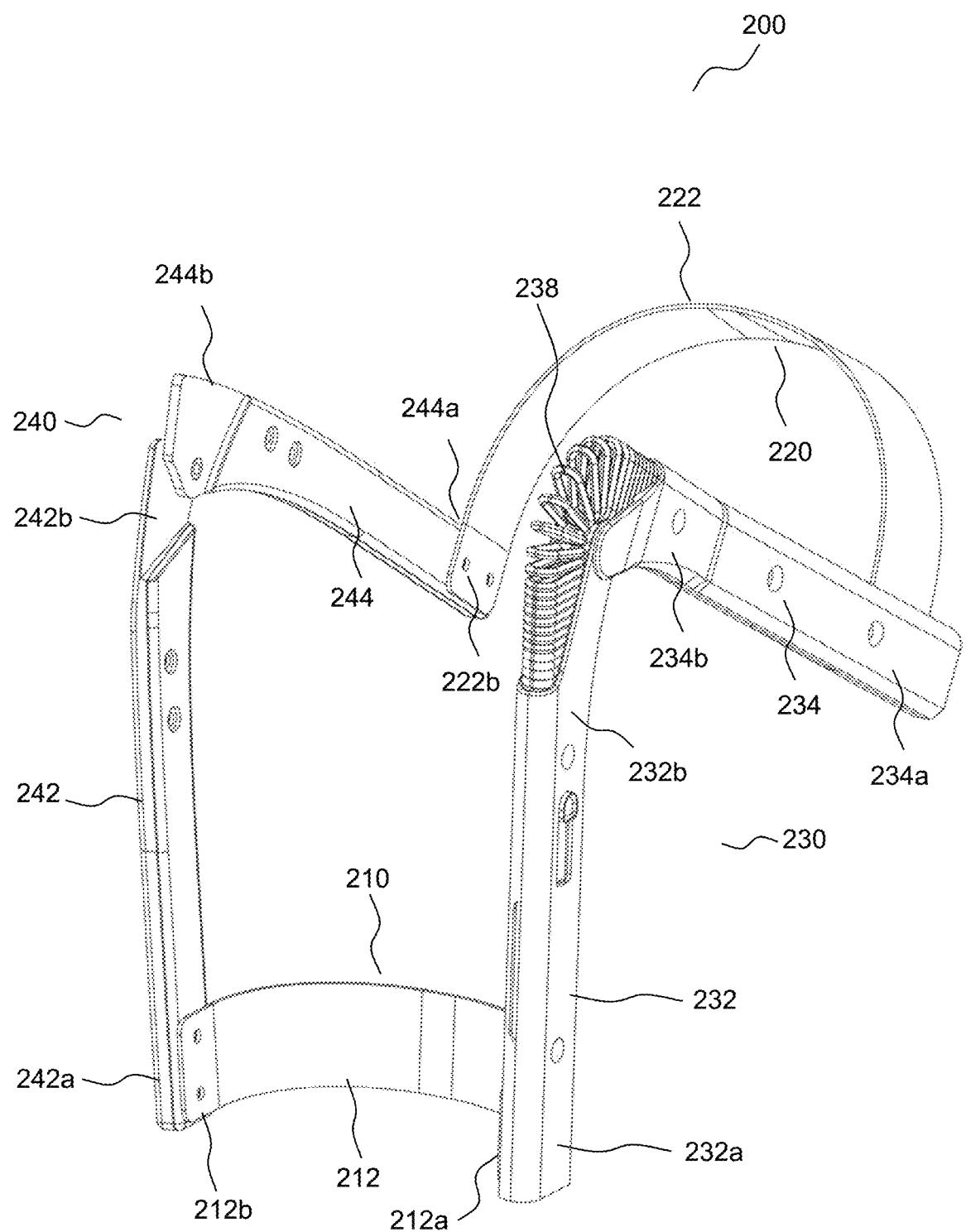

FIG. 2A and FIG. 2B show a device 200 for providing active assistance to a body joint between a first portion and a second portion of a body according to various embodiments. FIG. 2A shows the device 200 in a neutral state. FIG. 2B shows the device 200 in an active state to provide an active force which either acts against a bending motion of the body about the body joint or augments a straightening motion of the body about the body joint. The device 200 of FIG. 2A and FIG. 2B is shown as a knee orthosis or a knee brace for illustration purposes. It should be understood by those skilled in the art that various changes, modification, variation in form and detail may be made to adapt the features and limitations of the knee orthosis or knee brace into other types of orthosis or brace for other body joints without departing from the scope of the invention.

According to various embodiments, the device 200 may, similar to the device 100 of FIG. 1A and FIG. 1B, include a first attachment part 210 configured to hold the device 200 to the first portion of the body. According to various embodiments, the device 200 may, similar to the device 100 of FIG. 1A and FIG. 1B, include a second attachment part 220 configured to hold the device 200 to the second portion of the body.

According to various embodiments, each of the first and second attachment part 210, 220 may include a suitable securing arrangement to hold the device 200 to the first and second portions of the body 108 respectively. For example, as illustrated in FIG. 2A and FIG. 2B, each of the first attachment part 210 and the second attachment part 220 may include a combined rigid and flexible securing arrangement having a rigid element and a flexible element to form a single securing unit. According to various embodiments, each of the first attachment part 210 and the second attachment part 220 may include a curved-bracket 212, 222 (or a C-shaped frame or an arcuate structure) having a curvature extending from a first end 212a, 222a to a second end 212b, 222b respectively. According to various embodiments, the curved-bracket 212, 222 may be the rigid element of the combined rigid and flexible securing arrangement. According to various embodiments, each of the first attachment part 210 and the second attachment part 220 may further include a flexible element (not shown), such as a band or a strap or a flexible cuff or a belt or a strip or a Velcro or a sock or a bandage or a wrap or a sleeve, having an end of the flexible element fixedly coupled to either the first end 212a, 222a or the second end 212b, 222b of the curved-bracket 212, 222, and the other end of the flexible element configured for removably secured to the other end of the curved-bracket 212, 222.

According to various embodiments, the curvature of each of the curved-bracket 212, 222 of the first attachment part 210 and the second attachment part 220 may be shaped to correspond to a transverse contour of the first portion and the second portion of the body respectively. Accordingly, the first attachment part 210 and the second attachment part 220 may be fitted snugly to the first portion and the second portion of the body respectively for a secure attachment with the combined rigid and flexible secure arrangement.

According to various embodiments, when the device 200 is a knee orthosis or a knee brace, the first attachment part 210 may be configured to be secured to the lower leg and the second attachment part 220 may be configured to be secured to the upper leg for holding the device 200 to the leg, or vice versa. According to various embodiments, the curved-bracket 212 of the first attachment part 210 may be configured to be fitted to a calf of the lower leg and the curved-bracket 222 of the second attachment part 220 may be configured to be fitted to a thigh of the upper leg. According to various embodiments, the curved-bracket 212 of the first attachment part 210 may be shaped to be placed transversely across the calf of the lower leg and the curved-bracket 222 of the second attachment part 220 may be shaped to be placed transversely across the thigh of the upper leg.

According to various embodiments, the device 200 may, similar to the device 100 of FIG. 1A and FIG. 1B, include at least one spring module 230 interconnecting the first attachment part 210 and the second attachment part 220. Accordingly, the at least one spring module 230 may be extending between the first attachment part 210 and the second attachment part 220, and connecting the first attachment part 210 and the second attachment part 220 together. Hence, the first attachment part 210 may connected to the second attachment part 220 via the at least one spring module 230.

According to various embodiments, the at least one spring module 230 of the device 200 may, similar to the device 100 of FIG. 1A and FIG. 1B, include a first elongate link member 232 coupled to the first attachment part 210. According to various embodiments a first longitudinal end portion 232a of the first elongate link member 232 may be coupled to the first attachment part 210. According to various embodiments, the first elongate link member 232 may be coupled to the first attachment part 210 by screw, bolt and nut, clamp, clip, latch, hook, pin, or any other suitable fastener. Accordingly, the first elongate link member 232 and the first attachment part 210 may be configured to be capable of being coupled together and also capable of being detached from each other. Hence, the first elongate link member 232 may be removably coupled to the first attachment part 210.

According to various embodiments, the at least one spring module 230 of the device 200 may, similar to the device 100 of FIG. 1A and FIG. 1B, include a second elongate link member 234 coupled to the second attachment part 220. According to various embodiments, a first longitudinal end portion 234a of the second elongate link member 234 may be coupled to the second attachment part 220. According to various embodiments, the second elongate link member 234 may be coupled to the second attachment part 220 by screw, bolt and nut, clamp, clip, latch, hook, pin, or any other suitable fastener. Accordingly, the second elongate link member 234 and the second attachment part 220 may be configured to be capable of being coupled together and also capable of being detached from each other. Hence, the second elongate link member 234 may be removably coupled to the second attachment part 220.

According to various embodiments, the first elongate link member 232 and the second elongate link member 234 may be pivotably coupled to each other at a pivot joint 236 with a pivoting axis perpendicular to the first and second elongate link members 232, 234.

According to various embodiments, a second longitudinal end portion 232b of the first elongate link member 232 and a second longitudinal end portion 234b of the second elongate link member 234 may be pivotably coupled to each other at the pivot joint 236. According to various embodiments, the pivot joint 236 may be a pin joint or a hinge joint or a revolute joint. According to various embodiments, the second longitudinal end portion 234b of the second elongate link member 234 may include a pin protrusion 236a (see FIG. 3) inserted into a hole 236b (see FIG. 3) of the second longitudinal end portion 232b of the first elongate link member 232. According to various embodiments, the pin protrusion 236a may extend perpendicularly with respect to the second elongate link member 234. According to various embodiments, the first elongate link member 232 and the second elongate link member 234 may be pivotable relative to each other about the pivot joint 236 such that the first elongate link member 232 and the second elongate link member 234 may be moved relative to each other so as to form an angle with respect to each other at the pivot joint 236.

According to various embodiments, the first elongate link member 232 may include a first auxiliary securing arrangement (not shown) at the second longitudinal end portion 232b of the first elongate link member 232. According to various embodiments, the second elongate link member 234 may include a second auxiliary securing arrangement (not shown) at the second longitudinal end portion 234b of the second elongate link member 234. According to various embodiments, each of the first auxiliary securing arrangement and the second auxiliary securing arrangement may include a flexible element such as a band, a strap, a flexible cuff, a belt, a strip, a Velcro, a sock, a bandage, a wrap, a sleeve, etc. for securing the second longitudinal end portions 232b, 234b of the first and second elongate link member 232, 234 respectively to the first and second portions of the body via the first auxiliary securing arrangement and the second auxiliary securing arrangement respectively. According to various embodiments, the first auxiliary securing arrangement and the second auxiliary securing arrangement may facilitate relative pivoting motion of the first and second elongate link member 232, 234 about the pivot joint 236 when the first and second portions of the body bend relative to each other.

According to various embodiments, the at least one spring module 230 of the device 200 may, similar to the device 100 of FIG. 1A and FIG. 1B, include a coil spring 238 extending longitudinally between the first and second elongate link members 232, 234 and across the pivot joint 236. Accordingly, the coil spring 238 may extend across the pivoting axis of the pivot joint 236 so as to form a cross configuration with the pivoting axis of the pivot joint 236. According to various embodiments, the coil spring 238 may extend across the pivot joint 236 in a manner so as to be over the pivot joint 236, or under the pivot joint 236, or intersecting the pivoting axis of the pivot joint 236. According to various embodiments, the coil spring 238 may intersect the pivoting axis of the pivot joint 236 when the coil spring 238 extends transversely across an end of the pivot joint 236 in a manner so as to be abutting or adjacent to the end of the pivot joint 236. As shown, the coil spring 238 may extend across and over the pivot joint 236. According to various embodiments, a first end 238a of the coil spring 238 (see FIG. 5A, FIG. 5B, FIG. 7A and FIG. 7B) may be coupled to the first elongate link member 232 and a second end 238b of the coil spring 238 (see FIG. 5A, FIG. 5B, FIG. 7A and FIG. 7B) may be coupled to the second elongate link member 234. According to various embodiments, the coil spring 238 may be coupled to the first and second elongate link members 232, 234 respectively via welding, rivet, or hook. As shown, the at least one spring module 230 may include one coil spring 238 extending longitudinally between the first and second elongate link members 232, 234 and across the pivot joint 236. According to various other embodiments, the at least one spring module 230 may include one or more coil spring 238, each extending longitudinally between the first and second elongate link members 232, 234 and across the pivot joint 236.

According to various embodiments, the coil spring 238 may be arranged and disposed with respect to the first and second elongate link member 232, 234 in a manner such that a longitudinal axis of the coil spring 238 may extend from the first elongate link member 232 to the second elongate link member 234, whereby a first end segment of the coil spring 238 towards the first end 238a may be parallel to the first elongate link member 232 and a second end segment of the coil spring 238 towards the second end 238b may be parallel to the second elongate link member 234. According to various embodiments, a direction of a length of the coil spring 238 may be extending between the first and second elongate link members 232, 234 such that the coil spring 238 runs lengthwise from the first elongate link member 232 to the second elongate link member 234. According to various embodiments, the coil spring 228 may extend or run between the first and second elongate link members 232, 234 with the first end segment of the coil spring 238 running alongside at least a portion of a length of the first elongate link member 232, a mid-segment of the coil spring 238 running across the pivot joint 236 (e.g. over the pivot joint 236 as shown), and a second end segment of the coil spring 238 running alongside at least a portion of a length of the second elongate link member 234. According to various embodiments, when the first elongate link member 232 and the second elongate link member 234 forms an angle of 180° with respect to each other at the pivot joint 236, the coil spring 238 may be parallel to the first and second elongate link member 232, 234. Accordingly, the coil spring 238 may be aligned to the first and second elongate link member 232, 234 such that the first end segment of the coil spring 238 may be overlapping or side-by-side or alongside or coincide with at least a portion of a length of the first elongate link member 232, the second end segment of the coil spring 238 may be overlapping or side-by-side or alongside or coincide with at least a portion of a length of the second elongate link member 234, and the mid-segment of the coil spring 238 may lie across the pivot joint 236.

According to various embodiments, when the first and second ends 238a, 238b of the coil spring 238 are coupled to the first and second elongate link members 232, 234 respectively via welding and rivet, the first end 238a of the coil spring 238 may be permanently coupled to the first elongate link member 232 and the second end 238a of the coil spring 238 may be permanently coupled to the second elongate link member 232. According to various embodiments, when the first and second ends 238a, 238b of the coil spring 238 are coupled to the first and second elongate link members 232, 234 respectively via hook, the first and second ends 238a, 238b of the coil spring 238 may remain stationary or may not be movable relative to the first and second elongate link members 232, 234 respectively, and may also be capable of being detached from each other. Hence, the first and second ends 238a, 238b of the coil spring 238 may be removably coupled to the first and second elongate link members 232, 234 respectively.

According to various embodiments, with the first elongate link member 232 removably coupled to the first attachment part 210 and the second elongate link member 234 removably coupled to the second attachment part 220, the at least one spring module 230 may be modular with respect to the device 200 and may be easily replaceable with another spring module. According to various embodiments, the at least one spring module 230 may be removably coupled to the first attachment part 210 and the second attachment part 220. According to various embodiments, when the first end 238a of the coil spring 238 is removably coupled to the first elongate link member 232 (e.g. via hook) and the second end 238b of the coil spring 238 is removably coupled to the second elongate link member 234 (e.g. via hook), the coil spring 238 may be modular with respect to the at least one spring module 230 and may be easily replaceable with another coil spring. Accordingly, the coil spring 238 may be removably coupled (e.g. via hook) to the first and second elongate link members 232, 234 of the at least one spring module 230.

According to various embodiments, with the coil spring 238 arranged and applied in the at least one spring module 230 which interconnects the first attachment part 210 and the second attachment part 220, the coil spring 238 may provide a torque or a force, based on a lateral stiffness of the coil spring 238, against a first relative pivoting motion about the pivot joint 236 between the first and second elongate link members 232, 234 from a longitudinally aligned disposition of the first and second elongate link members 232, 234. The same torque or force provided by the coil spring 238, based on the lateral stiffness of the coil spring 238, may also augment a second relative pivoting motion about the pivot joint 236 between the first and second elongate link members 232, 234 to return to the longitudinally aligned disposition of the first and second elongate link members 232, 234 from an angled disposition.

According to various embodiments, the at least one spring module 230 may interconnects the curved-bracket 212 of the first attachment part 210 and the curved-bracket 222 of the second attachment part 220. According to various embodiments, the device may be free of other components interconnecting the curved-bracket 212 of the first attachment part 210 and the curved-bracket 222 of the second attachment part 220. Accordingly, the curved-bracket 212 of the first attachment part 210 and the curved-bracket 222 of the second attachment part 220 may be connected to each other only by the at least one spring module 230 without any other components. Hence, other than the at least one spring module 230 between the curved-bracket 212 of the first attachment part 210 and the curved-bracket 222 of the second attachment part 220, there may be a complete absence of any other components.

According to various embodiments, the first elongate link member 232 of the at least one spring module 230 may be coupled directly to the curved-bracket 212 of the first attachment part 210, and the second elongate link member 234 of the at least one spring module 230 may be coupled directly to the curved-bracket 222 of the second attachment part 220. According to various embodiments, as shown in FIG. 2A and FIG. 2B, the first longitudinal end portion 232a of the first elongate link member 232 may be coupled to the first end 212a of the curved-bracket 212 of the first attachment part 210. According to various embodiments, the first longitudinal end portion 234a of the second elongate link member 234 may be coupled to the first end 222a of the curved-bracket 222 of the second attachment part 220.

According to various embodiments, as shown in FIG. 2A and FIG. 2B, the device 200 may also include a linkage assembly 240 interconnecting the first attachment part 210 and the second attachment part 220. According to various embodiments, the linkage assembly 240 may interconnect the second end 212b of the curved-bracket 212 of the first attachment part 210 and the second end 222b of the curved-bracket 222 of the second attachment part 220. According to various embodiments, the device 200 may include one spring module 230 interconnecting the first end 212a of the curved-bracket 212 of the first attachment part 210 and the first end 222a of the curved-bracket 222 of the second attachment part 220 and one linkage assembly 240 interconnecting the second end 212b of the curved-bracket 212 of the first attachment part 210 and the second end 222*b* of the curved-bracket 222 of the second attachment part 220.

According to various embodiments, the linkage assembly 240 may include a first link rod 242 coupled to the first attachment part 210. According to various embodiments, the first link rod 242 may be coupled to the second end 212*b* of the curved-bracket 212 of the first attachment part 210. According to various embodiments, a first longitudinal end portion 242*a* of the first link rod 242 may be coupled to the first attachment part 210.

According to various embodiments, the linkage assembly 240 may include a second link rod 244 coupled to the second attachment part 220. According to various embodiments, the second link rod 244 may be coupled to the second end 222*b* of the curved-bracket 222 of the second attachment part 220. According to various embodiments, a first longitudinal end portion 244*a* of the second link rod 244 may be coupled to the second attachment part 220.

According to various embodiments, the first link rod 242 and the second link rod 244 may be pivotably coupled to each other at a pivot joint 246. According to various embodiments, a second longitudinal end portion 242*b* of the first link rod 242 and a second longitudinal end portion 244*b* of the second link rod 244 may be pivotably coupled to each other at the pivot joint 246. According to various embodiments, the pivot joint 246 may be a pin joint, a hinge joint, or a revolute joint. According to various embodiments, the second longitudinal end portion 244*b* of the first elongate link rod 242 may include a pin protrusion inserted into a hole of the second longitudinal end portion 244*b* of the second elongate link member 244. According to various embodiments, the pin protrusion may extend perpendicularly with respect to the first link rod 242. According to various embodiments, the first link rod 242 and the second link rod 244 may be pivotable relative to each other about the pivot joint 246 such that the first link rod 242 and the second link rod 244 may be moved relative to each other so as to form an angle with respect to each other at the pivot joint 246.

According to various embodiments, the pivot joint 246 of the linkage assembly 240 may be coaxial with the pivot joint 236 of the at least one spring module 230 between the first and second elongate link members 232, 234 of the at least one spring module 230. Accordingly, the linkage assembly 240 may be arranged and oriented parallel to the at least one spring module 230 in a manner such that the pivot joint 246 of the linkage assembly 240 may share a common pivoting axis with the pivot joint 236 of the at least one spring module 230. According to various embodiments, the first link rod 242 of the linkage assembly 240 may pivot relative to the second link rod 244 of the linkage assembly 240 in a synchronous manner with the relative pivoting motion between the first elongate link member 232 and the second elongate link member 234 of the at least one spring module 230.

Figure 3:
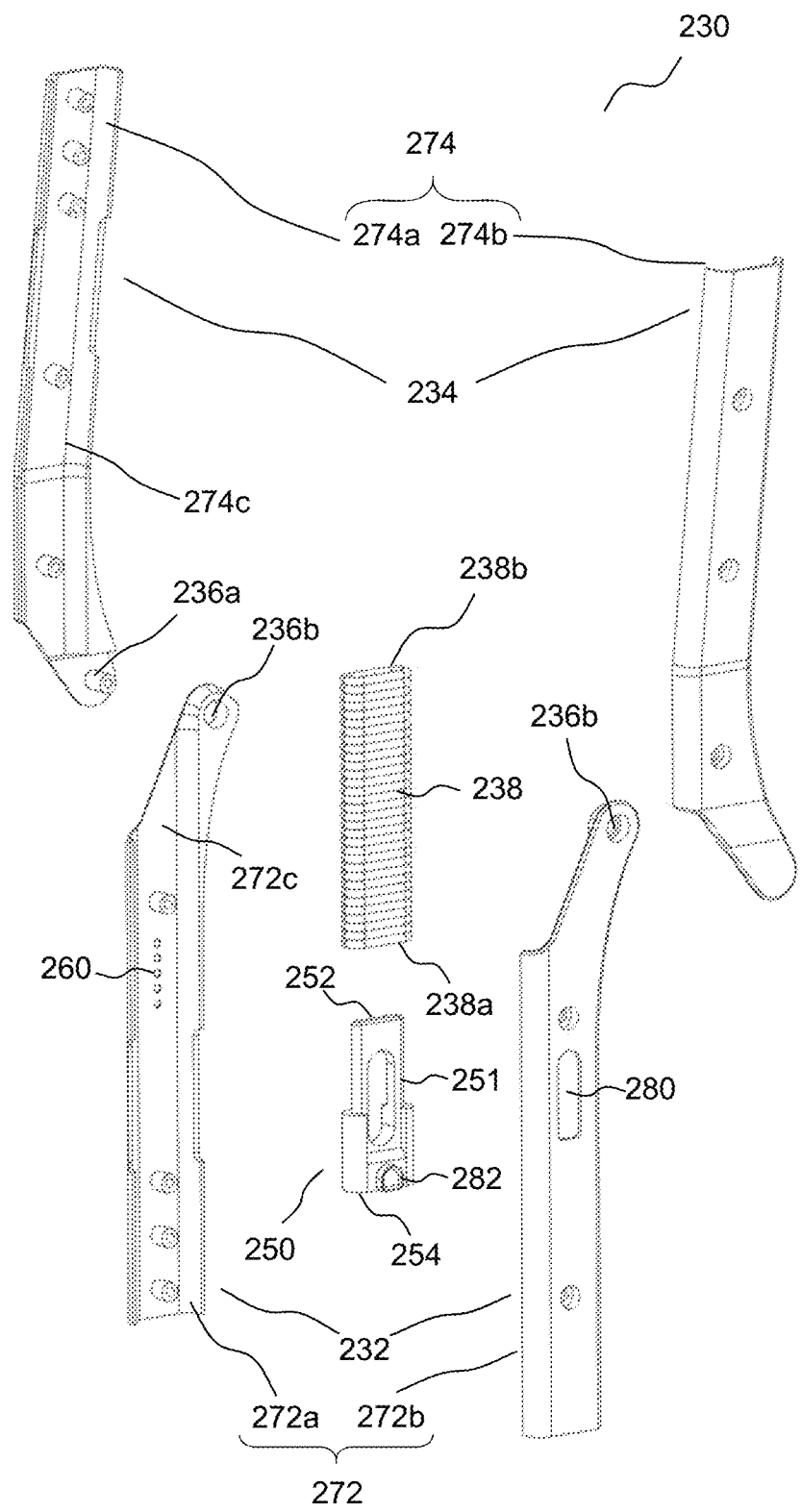
FIG. 3 shows an exploded view of the at least one spring module of the device of FIG. 2A and FIG. 2B according to various embodiments.
Figure 4A:
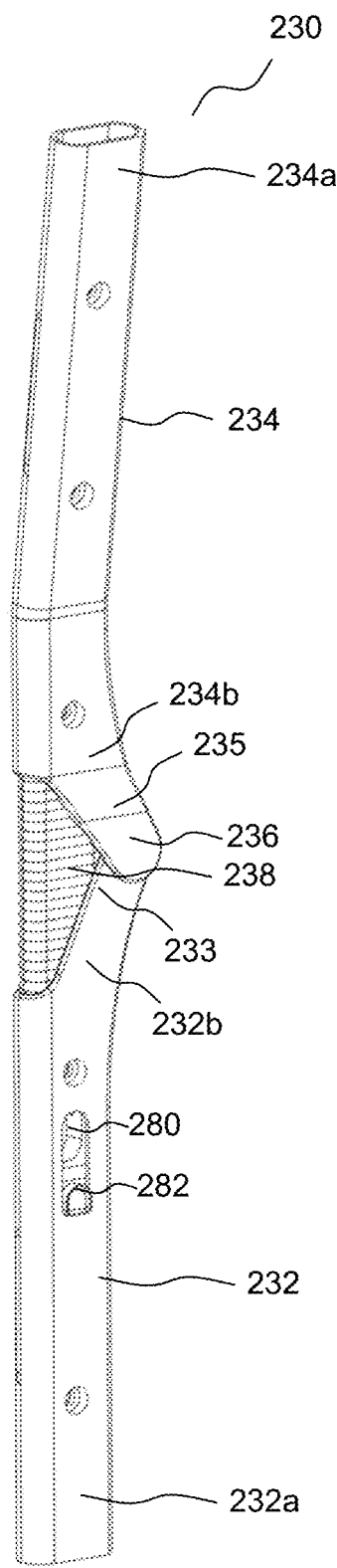
FIG. 4A and FIG. 4B show perspective views of the at least one spring module of the device of FIG. 2A and FIG. 2B in the longitudinally aligned disposition according to various embodiments.
Figure 4B:
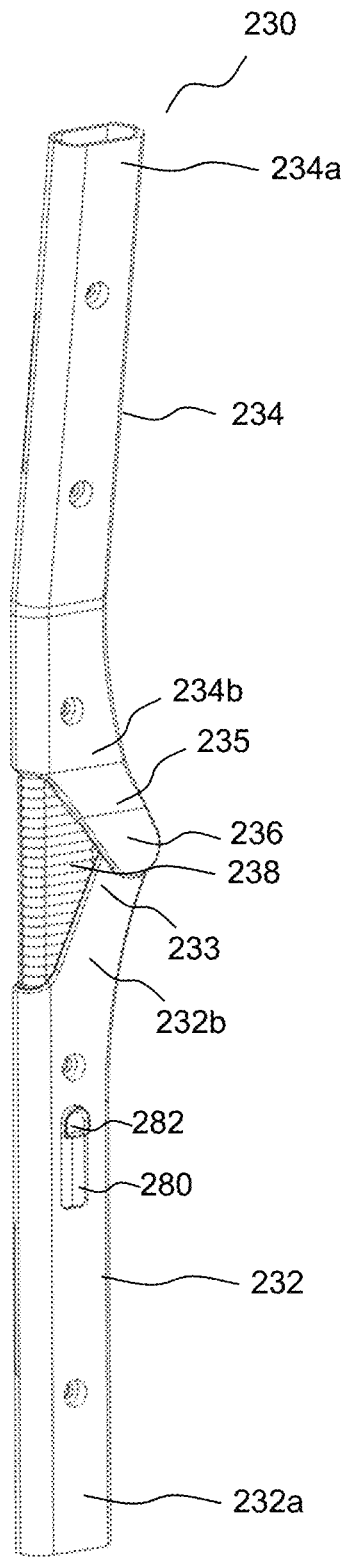
Figure 5A:
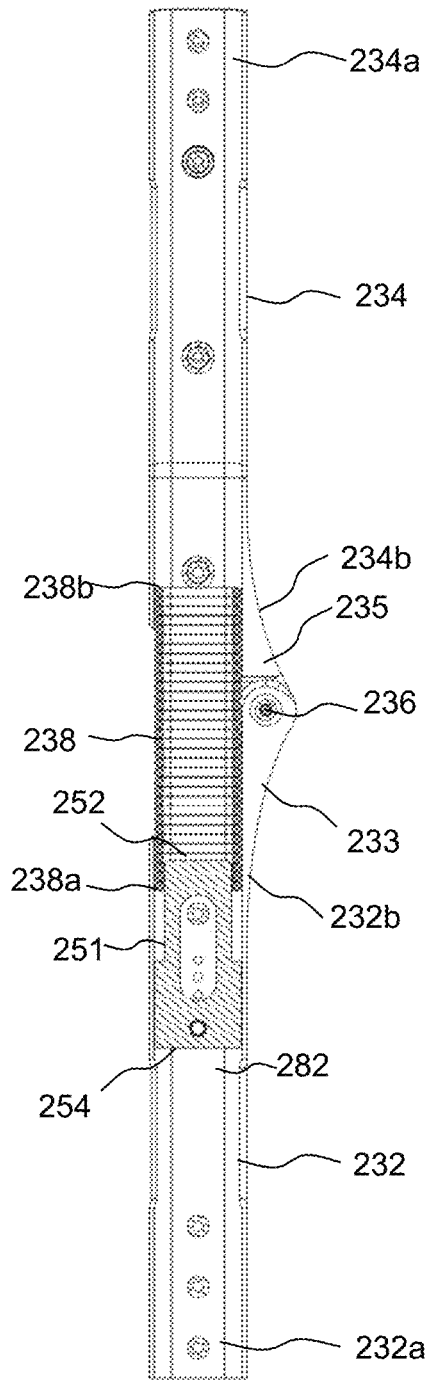
FIG. 5A and FIG. 5B show longitudinal cross-sectional views of the at least one spring module of the device of FIG. 2A and FIG. 2B in the longitudinally aligned disposition according to various embodiments.
Figure 5B:
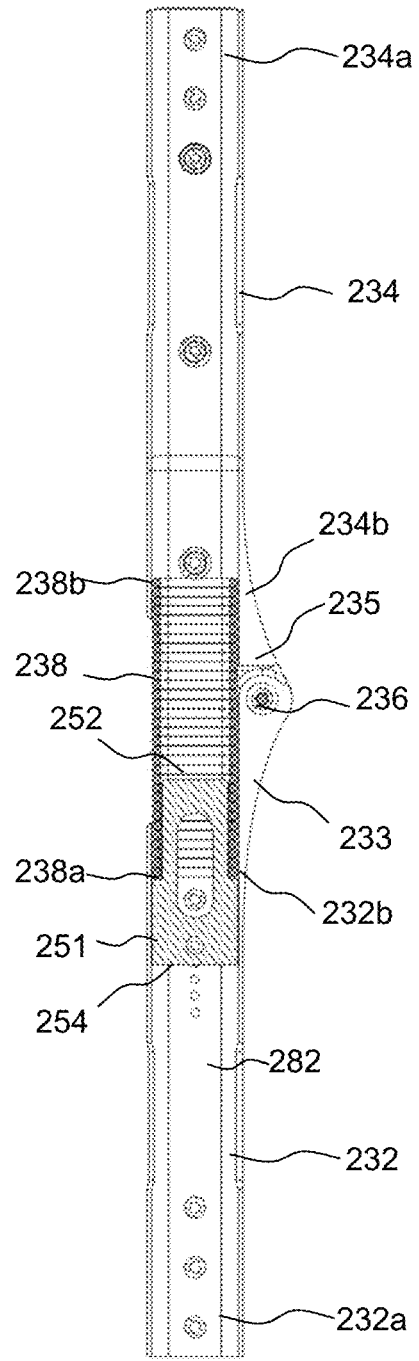
Figure 6B:
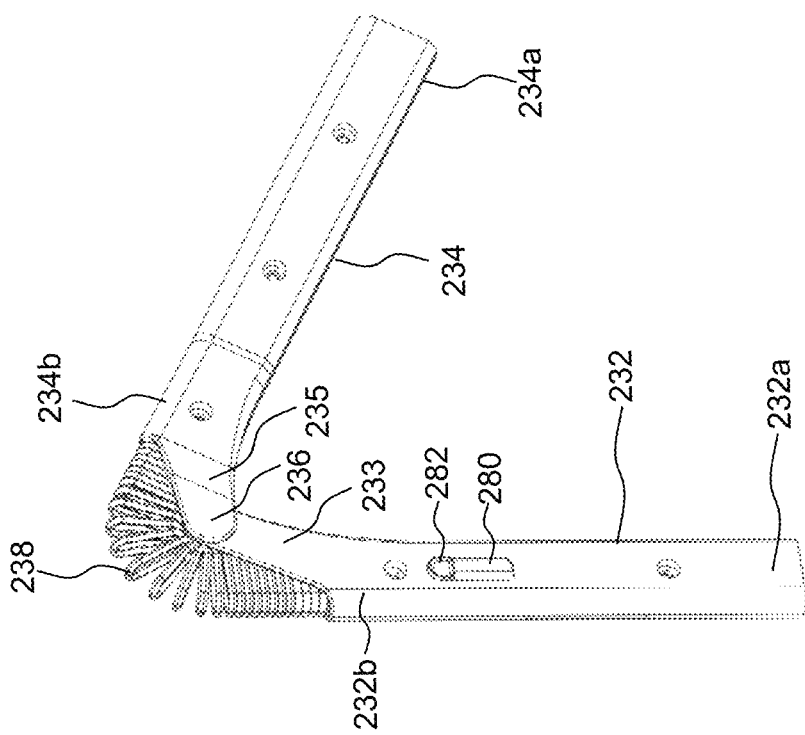
FIG. 6A and FIG. 6B show perspective views of the at least one spring module of the device of FIG. 2A and FIG. 2B with the first and second elongate link members 232, 234 pivoted relative to each other according to various embodiments.
Figure 6A:
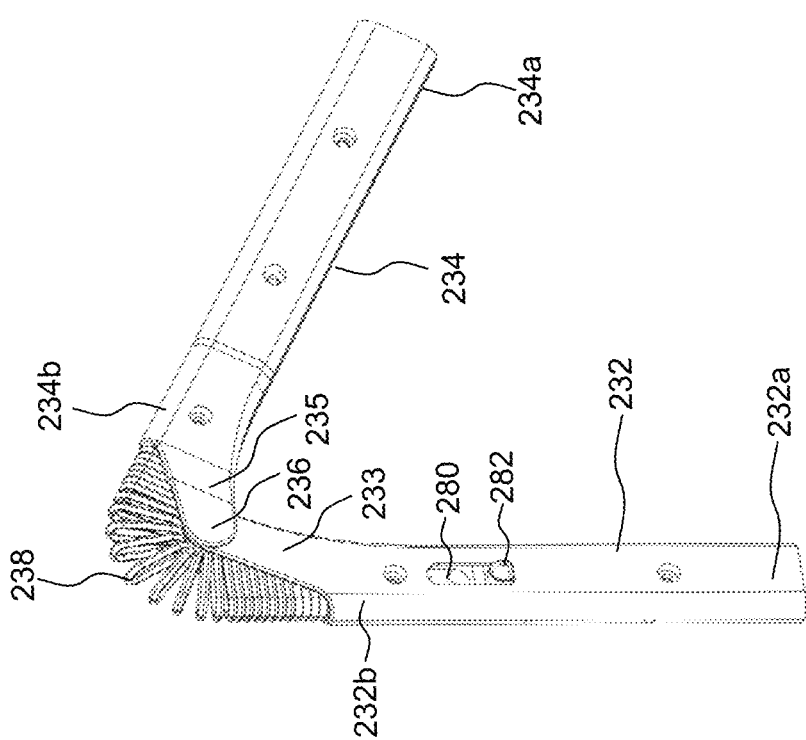
Figure 7B:
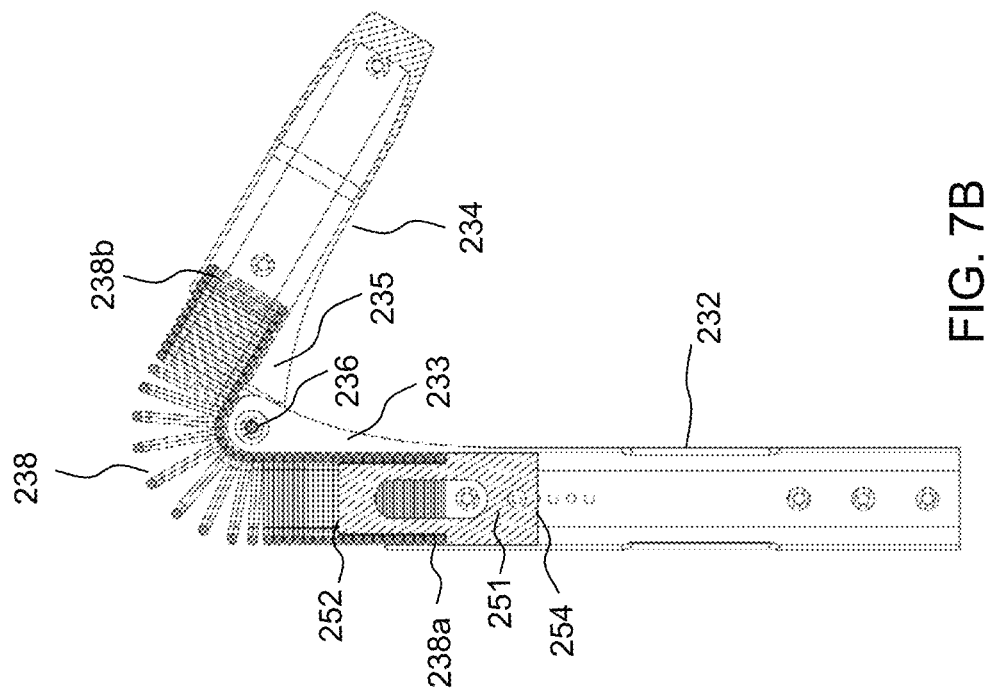
FIG. 7A and FIG. 7B show cross-sectional views of the at least one spring module as shown in FIG. 6A and FIG. 6B according to various embodiments.
Figure 7A:
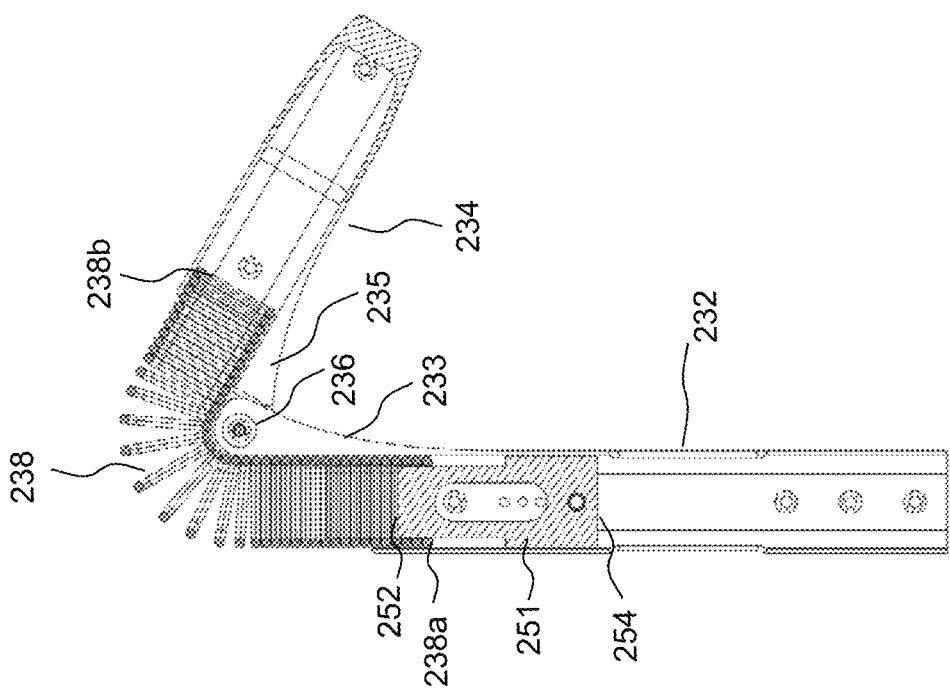

FIG. 3 shows an exploded view of the at least one spring module 230 of FIG. 2A and FIG. 2B according to various embodiments. FIG. 4A and FIG. 4B show perspective views of the at least one spring module 230 of FIG. 2A and FIG. 2B in the longitudinally aligned disposition according to various embodiments. FIG. 5A and FIG. 5B show longitudinal cross-sectional views of the at least one spring module 230 of FIG. 2A and FIG. 2B in the longitudinally aligned disposition (i.e. the spring module 230 being straightened) according to various embodiments. FIG. 6A and FIG. 6B show perspective views of the at least one spring module 230 of FIG. 2A and FIG. 2B with the first and second elongate link members 232, 234 pivoted relative to each other (i.e. the spring module 230 being bent) according to various embodiments. FIG. 7A and FIG. 7B show cross-sectional views of the at least one spring module 230 as shown in FIG. 6A and FIG. 6B according to various embodiments.

According to various embodiments, as shown in FIG. 3, FIG. 5A and FIG. 5B, and FIG. 7A and FIG. 7B, the at least one spring module 230 may include a slidable coil-spring-retaining-member 250 at the first elongate link member 232. According to various embodiments, the slidable coil-spring-retaining-member 250 may be disposed at or fitted to the first elongate link member 232. According to various embodiments, the coil-spring-retaining-member 250 may be slidable longitudinally relative to the first elongate link member 232. Accordingly, the coil-spring-retaining-member 250 may be slidable along a length of the first elongate link member 232. According to various embodiments, with the first end 238*a* of the coil spring 238 coupled to the first elongate link member 232, the coil-spring-retaining-member 250 may be slidable along the first elongate link member 232 to engage and retain a portion of the length of the coil spring 238 from the first end 238*a* of the coil spring 238. Accordingly, the portion of the length of the coil spring 238, from the first end 238*a* of the coil spring 238 towards the second end 238*b*, that is engaged and retained by the coil-spring-retaining-member 250 may be varied by sliding the coil-spring-retaining-member 250 relative to the first elongate link member 232. According to various embodiments, with the coil-spring-retaining-member 250 in engagement and retaining the portion of the length of the coil spring 238, said portion of the length of the coil spring 238 may not be subjected or exposed to the pivoting motion between the first and second elongate link members 232, 234. Accordingly, the portion of the length of the coil spring 238 may be constrained or may not be effective in acting against the first relative pivoting motion between the first and second elongate link members 232, 234 from the longitudinally aligned disposition of the first and second elongate link members 232, 234, and/or augmenting the second relative pivoting motion between the first and second elongate link member 232, 234 to return to the longitudinally aligned disposition. According to various embodiments, the portion of the length of the coil spring 238 engaged and retained by the coil-spring-retaining-member 250 may correspondingly reduce an effective length of the coil spring 238 (or an effective number of coils of the coil spring 238) subjected or exposed to the pivoting motion between the first and second elongate link members 232, 234.

According to various embodiments, the coil spring 238 may have a higher effective lateral stiffness when the effective length of the coil spring 238 is shorter. Accordingly, by sliding the coil-spring-retaining-member 250 along the first elongate link member 232 to engage and retain a portion of the length of the coil spring 238 from the first end 238*a* of the coil spring 238, the effective length of the coil spring 238 may be reduced and, thus, the effective lateral stiffness of the coil spring 238 may be higher. With a higher effective lateral stiffness, the coil spring 238 may provide a greater force or torque to act against the first relative pivoting motion between the first and second elongate link members 232, 234 from the longitudinally aligned disposition of the first and second elongate link members 232, 234, and/or to augment the second relative pivoting motion between the first and second elongate link member 232, 234 to return to the longitudinally aligned disposition. According to various embodiments, the force or torque provided by the at least one spring module 230 may be varied by sliding the coil-spring-retaining-member 250 relative to the first elongate link member 232 to vary the portion of the length of the coil spring 238, from the first end 238a of the coil spring 238 towards the second end 238b, engaged and retained by the coil-spring-retaining-member 250.

According to various embodiments, as shown in FIG. 3, FIG. 5A, FIG. 5B, FIG. 7A, and FIG. 7B, the coil-spring-retaining-member 250 may be in the form of a coil-spring-retaining-insert 251 slidable relative to the first elongate link member 232. According to various embodiments, a free end 252 of the coil-spring-retaining-insert 251 may be slidably inserted into the coil spring 238 from the first end 238a thereof. According to various embodiments, by sliding the coil-spring-retaining-insert 251 relative to the first elongate link member 232, a length of the coil-spring-retaining-insert 251, from a free end 252 of the coil-spring-retaining-insert 251 towards an opposite end 254, that is inserted within the coil spring 238 may be varied.

According to various embodiments, by varying the length of the coil-spring-retaining-insert 251 slidably inserted within the coil spring 238, the portion of the length of the coil spring 238 engaged and retained by the coil-spring-retaining-insert 251 may by varied so as to vary the effective length of the coil spring 238 (or an effective number of coils of the coil spring 238) subjected or exposed to the pivoting motion between the first and second elongate link members 232, 234.

According to various embodiments, the at least one spring module 230 may include a locking mechanism 260 to lock the slidable coil-spring-retaining-member 250 to the first elongate link member 232. According to various embodiments, the locking mechanism 260 may be any suitable locking mechanism, for example, a spring-loaded ball type locking mechanism whereby the first elongate link member 232 includes a series of holes or indentations along its length and the slidable coil-spring-retaining-member 250 include a spring-loaded ball to engage with the holes or indentations; or a spring-loaded plunger type locking mechanism whereby the first elongate link member 232 includes a series of holes or indentations along its length and the slidable coil-spring-retaining-member 250 include a spring-loaded ball to engage with the holes or indentations; or a ratchet type locking mechanism whereby the first elongate link member 232 includes a series of teeth along its length and the slidable coil-spring-retaining-member 250 include a spring-loaded pawl to engage with the teeth.

According to various embodiments, the second longitudinal end portion 232b of the first elongate link member 232 may include a diagonal arm 233 extending therefrom. According to various embodiments, the second longitudinal end portion 234b of the second elongate link member 234 may include a diagonal arm 235 extending therefrom. According to various embodiments, a tip portion 233a of the diagonal arm 233 of the first elongate link member 232 may be pivotably coupled to a tip portion 235a of the diagonal arm 235 of the second elongate link member 234 in a manner so as to form the pivot joint 236 immediately adjacent the mid-segment of the coil spring 238 when the coil spring 238, which is extending between the first and second elongate link members 232, 234, is aligned with the first and second elongate link members. According to various embodiments, the diagonal arms 233, 235 of the first and second elongate link members may allow the coil spring 238 to be extending in a straight line with the first and second elongate link members 232, 234 when in the longitudinal aligned disposition.

According to various embodiments, the mid-segment of the coil spring 238 may be adjacent and abutting the pivot joint 236. According to various embodiments, the pivot joint 236 may serve as a bending support to prop or hold up the mid-segment of the coil spring 238 for bending the coil spring 238 during pivoting motion of the first and second elongate link members 232, 234 about the pivot joint 236.

According to various embodiments, the first elongate link member 232 may include a hollow frame 272 (or hollow structure) wherein the first end 238a of the coil spring 238 may be inserted into the first elongate link member 232 and coupled to an inner wall surface 272c of the first elongate link member 232. According to various embodiments, the hollow frame 272 of the first elongate link member 232 may include an empty space extending longitudinally along the first elongate link member 232. According to various embodiments, the first end 238a of the coil spring 238 may be inserted into an opening of the hollow frame 272 of the first elongate link member 232 at the second longitudinal end portion 232a of the first elongate link member 232.

According to various embodiments, the hollow frame 272 of the first elongate link member 232 may be formed by two elongate shell parts 272a, 272b joined together lengthwise. According to various embodiments, the two elongate shell parts 272a, 272b may correspond to the hollow frame 272 of the first elongate link member 232 being divided and separated longitudinally. According to various embodiments, the two elongate shell parts 272a, 272b may be joined together via screw, bolt and nut, clamp, clip, latch, hook, pin, or any other suitable fastener.

According to various embodiments, the second elongate link member 234 may include a hollow frame 274 (or hollow structure) wherein the second end 238b of the coil spring 238 may be inserted into the second elongate link member 234 and coupled to an inner wall surface 274c of the second elongate link member 234. According to various embodiments, the hollow frame 274 of the second elongate link member 234 may include an empty space extending longitudinally along the second elongate link member 234. According to various embodiments, the second end 238b of the coil spring 238 may be inserted into an opening of the hollow frame 274 of the second elongate link member 234 at the second longitudinal end portion 234a of the second elongate link member 234.

According to various embodiments, the hollow frame 274 of the second elongate link member 234 may be formed by two elongate shell parts 274a, 274b joined together lengthwise. According to various embodiments, the two elongate shell parts 274a, 274b may correspond to the hollow frame 274 of the second elongate link member 234 being divided and separated longitudinally. According to various embodiments, the two elongate shell parts 274a, 274b may be joined together via screw, bolt and nut, clamp, clip, latch, hook, pin, or any other suitable fastener.

According to various embodiments, when the coil-spring-retaining-member 250 is the coil-spring-retaining-insert 251 as shown in FIG. 3, the coil-spring-retaining-insert 251 may be slidable inside or within the hollow frame 272 of the first elongate link member 232.

According to various embodiments, the coil-spring-retaining-insert 251 may be enclosed inside or within the hollow frame 272 of the first elongate link member 232 in a manner such that the coil-spring-retaining-insert 251 may be slidable along the empty space extending longitudinally along the first elongate link member 232. According to various embodiments, the first elongate link member 232 may include a longitudinal slot 280 along a wall portion of the hollow frame 272 of the first elongate link member 232. According to various embodiments, the longitudinal slot 280 may be extending lengthwise along the wall portion of one of the two elongate shell parts 272a, 272b of the hollow frame 272 of the first elongate link member 232. According to various embodiments, the coil-spring-retaining-insert 251 may include a protrusion 282 extenting from the coil-spring-retaining-insert 251 and through the longitudinal slot 280.

According to various embodiments, the protrusion 282 of the coil-spring-retaining-insert 251 may be extending perpendicularly from a surface of the coil-spring-retaining-insert 251 in a manner such that protrusion 282 penetrates the wall portion of the one of the two elongate shell parts 272a, 272b of the hollow frame 272 of the first elongate link member 232 through the longitudinal slot 280.

Figure 8A:
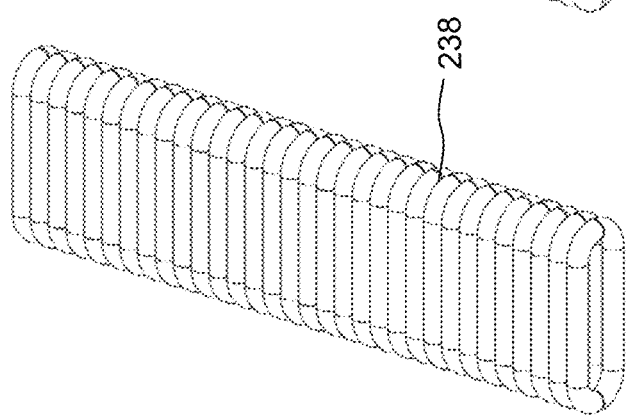
FIG. 8A to FIG. 8C shows various examples of the coil spring of the device of FIG. 2A to FIG. 7B according to various embodiments.
Figure 8A:
Figure 8B:
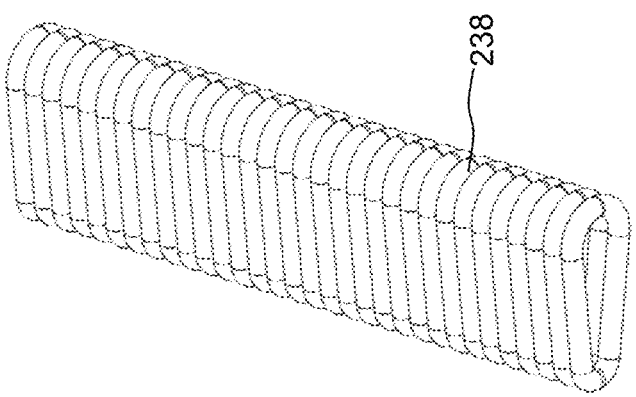
Figure 8B:
Figure 8C:
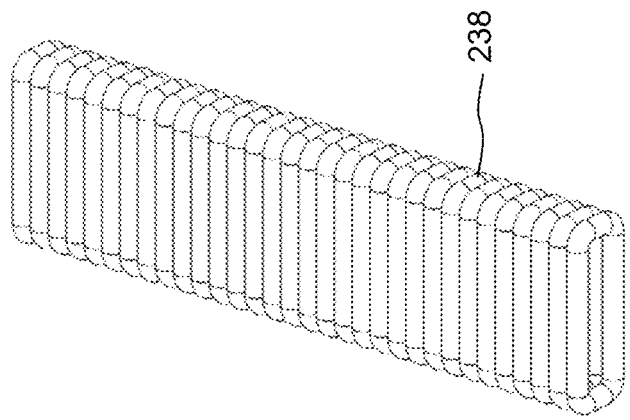
Figure 8C:

FIG. 8A to FIG. 8C shows various examples of the coil spring 238 of FIG. 2A to FIG. 7B according to various embodiments. According to various embodiments, the coil spring 238 may include, but not limited to, a pill-shaped coil spring as shown in FIG. 8A, or a wedged-shape coil spring as shown in FIG. 8B, or a rectangular-shaped coil spring as shown in FIG. 8C. According to various embodiments, each coil of the coil spring 238 may include an elongate shape, such as, but not limited to, pill-shaped, wedged-shaped, or rectangular-shaped. According to various embodiments, each coil of the coil spring 238 may be in contact with each other in the original unloaded state.

According to various embodiments, a device (not shown) for providing assistance to a body joint between a first portion and a second portion of a body may include two spring modules interconnecting the first attachment part and the second attachment part. Accordingly, the two spring modules may be extending between a first attachment part and a second attachment part, and connecting the first attachment part and the second attachment part together. Hence, the first attachment part may be connected to the second attachment part via the two spring modules. According to various embodiments, the device may include a first spring module interconnecting a first end of a curved-bracket of a first attachment part (similar to that of the device 200) and a first end of a curved-bracket of the second attachment part. According to various embodiments, the second spring module may be interconnecting a second end of the curved-bracket of the first attachment part and a second end of the curved-bracket of the second attachment part.

According to various embodiments, each of the first and second spring modules may, similar to that of the device 100 of FIG. 1A and FIG. 1B and the device 200 of FIG. 2A to FIG. 7B, include a first elongate link member coupled to the first attachment part, and a second elongate link member coupled to the second attachment part. According to various embodiments, the first elongate link member and the second elongate link member of the first and second spring modules may respectively be pivotably coupled to each other at a pivot joint, wherein the pivot joints of the first and second spring modules may be coaxial, i.e. sharing a common pivoting axis.

According to various embodiments, each of the first and second spring modules, may, similar to that of the device 100 of FIG. 1A and FIG. 1B and the device 200 of FIG. 2A to FIG. 7B, include a coil spring extending longitudinally between the first elongate link member and the second elongate link member and across the pivot joint. According to various embodiments, a first end of each of the coil spring may respectively be coupled to the first elongate link member, and a second end of each of the coil spring may respectively be coupled to the second elongate link member.

According to various embodiments, other than the first and second spring modules, the device with the two spring modules may be free of other components, e.g. the linkage assembly 240 of the device 200 of FIG. 2A to FIG. 7B, interconnecting the first attachment part and the second attachment part. According to various embodiments, the device may include only the first and second spring modules interconnecting the first attachment part and the second attachment part without any other components interconnecting therebetween.

Figure 9:
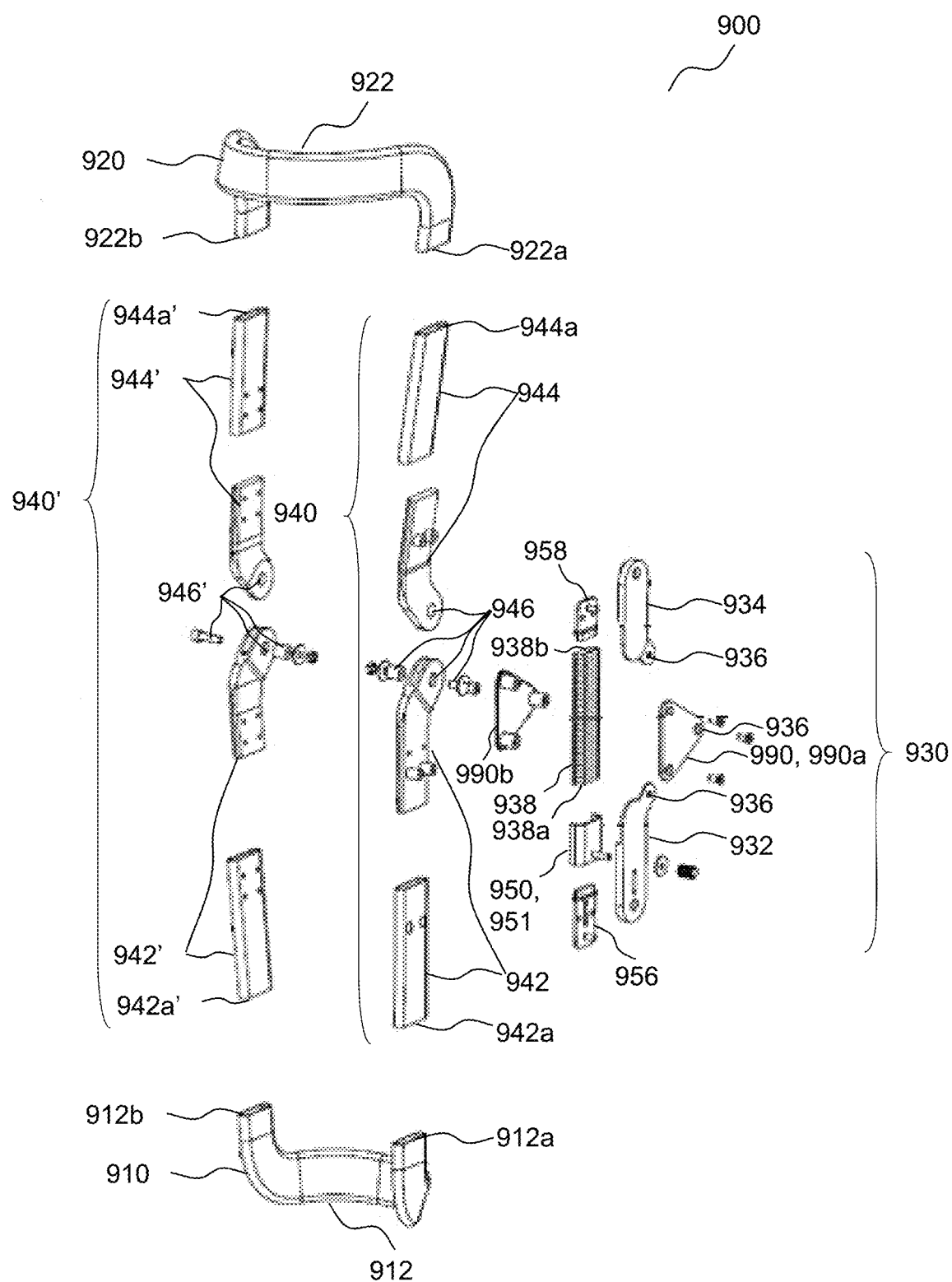
FIG. 9 shows an exploded view of a device for providing active assistance to a body joint between a first portion and a second portion of a body according to various embodiments.

FIG. 9 shows an exploded view of a device 900 for providing active assistance to a body joint between a first portion and a second portion of a body according to various embodiments. The device 900 of FIG. 9, similar to the device 200 of FIG. 2A to FIG. 7B, is shown as a knee orthosis or a knee brace for illustration purposes. It should be understood by those skilled in the art that various changes, modification, variation in form and detail may be made to adapt the features and limitations of the knee orthosis or knee brace into other types of orthosis or brace for other body joints without departing from the scope of the invention.

According to various embodiments, the device 900 may, similar to the device 100 of FIG. 1A and FIG. 1B and the device 200 of FIG. 2A to FIG. 7B 9, include a first attachment part 910 configured to hold the device 900 to the first portion of the body. According to various embodiments, the device 900 may, similar to the device 100 of FIG. 1A and FIG. 1B and the device 200 of FIG. 2A to FIG. 7B, include a second attachment part 920 configured to hold the device 900 to the second portion of the body. According to various embodiments, each of the first attachment part 910 and the second attachment part 920 may, similar to that of the device 100 of FIG. 1A and FIG. 1B and the device 200 of FIG. 2A to FIG. 7B, include a curved-bracket 912, 922 (or a C-shaped frame or an arcuate structure) having a curvature extending from a first end 912a, 922a to a second end 912b, 922b respectively.

According to various embodiments, the device 900 may include two linkage assemblies 940, 940' interconnecting the first attachment part 910 and the second attachment part 920. Accordingly, the two linkage assemblies 940, 940' may interconnect first attachment part 910 and the second attachment part 920. Hence, the first attachment part 910 may be connected to the second attachment part 920 via the two linkage assemblies 940, 940'. According to various embodiments, the device 900 may include a first linkage assembly 940 interconnecting the first end 912a of the curved-bracket 912 of the first attachment part 910 and the first end 922a of the curved-bracket 922 of the second attachment part 920. According to various embodiments, the second linkage assembly 940' may be interconnecting the second end 912b of the curved-bracket 912 of the first attachment part 910 and the second end 922b of the curved-bracket 922 of the second attachment part 920.

According to various embodiments, each of the first and second linkage assemblies 940, 940' may include a first link 942, 942' coupled to the first attachment part 910. According to various embodiments, a first longitudinal end portion 942a, 942a' of the first link 942, 942' of each of the first and second linkage assemblies 940, 940' may be coupled to the first attachment part 910. According to various embodiments, each of the first link 942, 942' of the first and second linkage assemblies 940, 940' may include two parts joined together to form the first link 942, 942' respectively.

According to various embodiments, each of the first and second linkage assemblies 940, 940' include a second link 944, 944' coupled to the second attachment part 920. According to various embodiments, a first longitudinal end portion 944a, 944a' of the second link 944, 944' may be coupled to the second attachment part 920. According to various embodiments, each of the second link 944, 944' of the first and second linkage assemblies 940, 940' may include two parts joined together to form the second link 944, 944' respectively.

According to various embodiments, the first link 942, 942' and the second link 944, 944' of the first and second linkage assemblies 940, 940' respectively may be pivotably coupled to each other at a pivot joint 946, 946'. According to various embodiments, the pivot joints 946, 946' of the first and second linkage assemblies 940, 940' may be coaxial, i.e. sharing a common pivoting axis.

According to various embodiments, the device 100 may, similar to the device 100 of FIG. 1A and FIG. 1B and the device 200 of FIG. 2A to FIG. 7B, include at least one spring module 930 interconnecting the first attachment part 910 and the second attachment part 920. According to various embodiments, the at least one spring module 930 may be interconnecting the first attachment part 910 and the second attachment part 920 by attaching to one of the two linkage assemblies 940, 940'. According to various embodiments, the at least one spring module 930 may be attached to the first linkage assembly 940 so as to interconnect the first attachment part 910 and the second attachment part 920.

According to various embodiments, the at least one spring module 930 may, similar to that of the device 100 of FIG. 1A and FIG. 1B and the device 200 of FIG. 2A to FIG. 7B, include a first elongate link member 932 coupled to the first attachment part 910. According to various embodiments, the first elongate link member 932 may be coupled to the first attachment part 910 via the first link 942 of the first linkage assembly 940. According to various embodiments, the second elongate link member 934 may be coupled to the second attachment part 920 via the second link 944 of the first linkage assembly 940. Accordingly, the first and second elongate link members 932, 934 of the at least one spring module 930 may be respectively coupled to the first and second links 942, 944 of the first linkage assembly 940. According to various embodiments, the first elongate link member 932 and the second elongate link member 934 of at least one spring module 930 may respectively be pivotably coupled to each other at a pivot joint 936. According to various embodiments, the pivot joint 936 of the at least one spring module 930 may be coaxial, i.e. sharing a common pivoting axis, with the pivot joint 946, 946' of the first and second linkage assemblies 940, 940'. According to various embodiments, the pivot joint 936 of the at least one spring module 930 may be coupled or joined to the pivot joint 946 of the first linkage assembly 940.

According to various embodiments, the at least one spring module 930 may, similar to that of the device 100 of FIG. 1A and FIG. 1B and the device 200 of FIG. 2A to FIG. 7B, include a coil spring 938 extending longitudinally between the first elongate link member 932 and the second elongate link member 934 and across the pivot joint 936. According to various embodiments, a first end 938a of the coil spring 938 may be coupled to the first elongate link member 932 via a first spring-coupler 956 and a second end 938b of the coil spring 938 may be coupled to the second elongate link member 934 via a second spring-coupler 958.

According to various embodiments, the at least one spring module 930 may include a triangular fulcrum arrangement 990 at the pivot joint 936. According to various embodiments, a corner of the triangular fulcrum arrangement 990 may be coupled to the pivot joint 936. According to various embodiments, the triangular fulcrum arrangement 990 may include two triangular plates 990a, 990b joined or coupled together at all three corners of the triangular fulcrum arrangement 990. According to various embodiments, the coil spring 938 may be inserted through adjacent sides of the triangular fulcrum arrangement 990 with respect to the corner of the triangular fulcrum arrangement 990 coupled to the pivot joint 936 in a manner such at the mid-segment of the coil spring 938 may be adjacent and abutting the corner of the triangular fulcrum arrangement 990 coinciding with the pivot joint 936. According to various embodiments, the triangular fulcrum arrangement 990 may serve as a bending support to prop or hold up the mid-segment of the coil spring 938 for bending the coil spring 938 during pivoting motion of the first and second elongate link members 932, 934 about the pivot joint 936.

According to various embodiments, the at least one spring module 930 may, similar to that of the device 200 of FIG. 2A to FIG. 7B, include a slidable coil-spring-retaining-member 950 at the first elongate link member 932. According to various embodiments, the coil-spring-retaining-member 950 may be in the form of a coil-spring-retaining-bracket 951 slidable relative to the first elongate link member 932. According to various embodiments, the coil-spring-retaining-bracket 951 may slide over the coil spring 938 from the first end 938a thereof for engaging and retaining a portion of a length of the coil spring 938. According to various embodiments, by sliding the coil-spring-retaining-bracket 951 relative to the first elongate link member 932, the coil-spring-retaining-bracket 951 may slide over a portion of a length of the coil spring 938, from the first end 938a of the coil spring 938 towards a second end 938b. According to various embodiments, by varying the portion of the length of the coil spring 938 engaged and retained by the coil-spring-retaining-bracket 951, an effective length of the coil spring 938 (or an effective number of coils of the coil spring 938), which is subjected or exposed to the pivoting motion between the first and second elongate link members 932, 934, may be varied.

Figure 10:
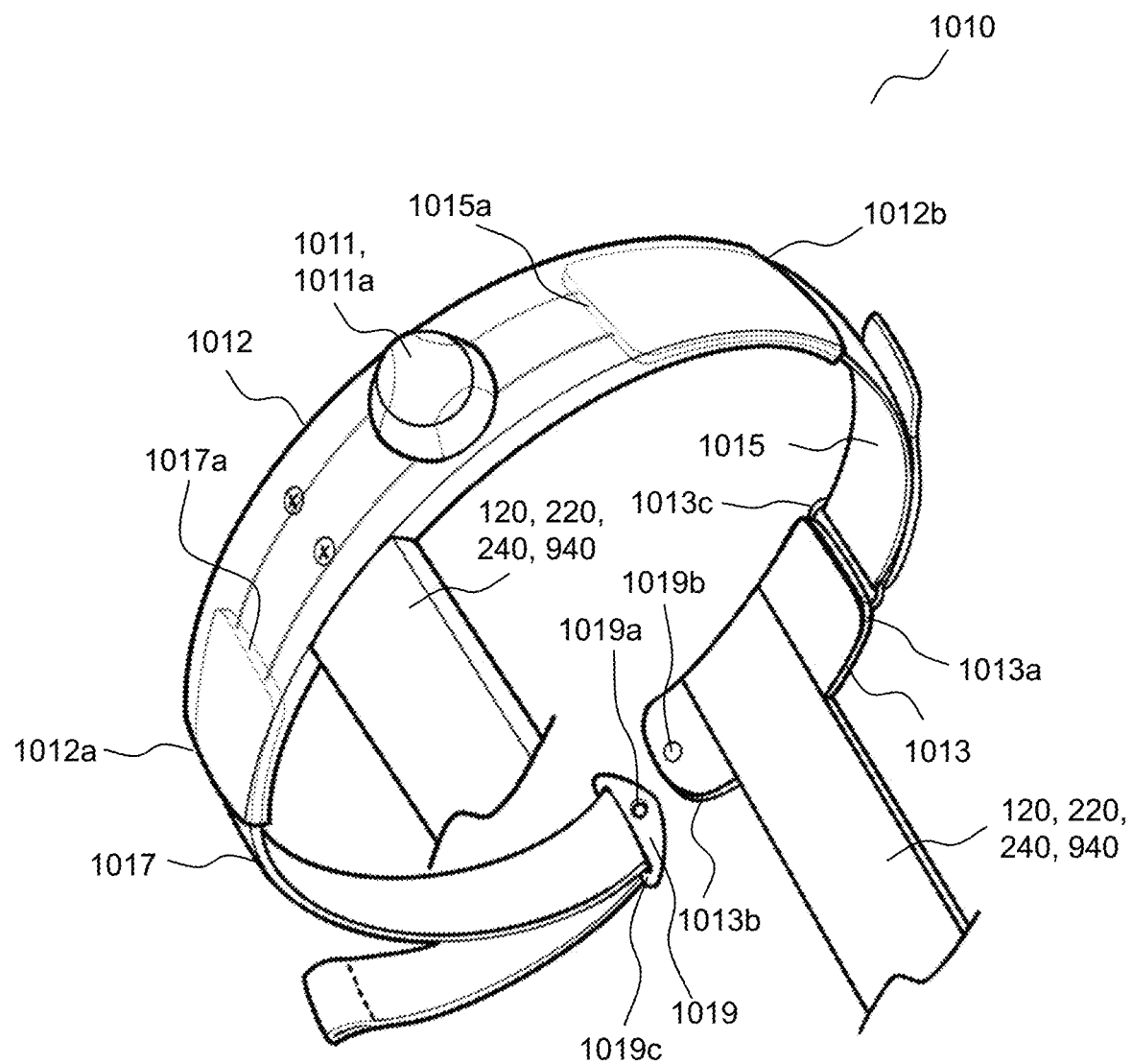
FIG. 10 shows a variant of an attachment part of a device for providing active assistance to a body joint between a first portion and a second portion of a body according to various embodiments.

FIG. 10 shows a variant of an attachment part 1010 of a device for providing active assistance to a body joint between a first portion and a second portion of a body according to various embodiments. According to the various embodiments, the attachment part 1010 may be incorporated into or combined with the device 100, 200, 900 as previously described to form the first and second attachment parts 110, 120, 210, 220, 910, 920 respectively.

According to various embodiments, the attachment part 1010 may be a combined rigid and flexible securing arrangement. According to various embodiments, the attachment part 1010 may include a first curved-bracket 1012 and a second curved bracket 1013. According to various embodiments, the first curved-bracket 1012 (or a C-shaped frame or an arcuate structure) may have a curvature extending from a first end 1012a to a second end 1012b respectively. According to various embodiments, the second curved-bracket 1013 (or a C-shaped frame or an arcuate structure) may have a curvature extending from a first end 1013a to a second end 1013b respectively. Accordingly, the first curved-bracket 1012 and the second curved bracket 1013 may be the rigid part of the combined rigid and flexible securing arrangement.

According to various embodiments, the attachment part 1010 may include a first flexible member 1015 and a second flexible member 1017. According to various embodiments, each of the first and second flexible members 1015, 1017 may include, but not limited to, a band, a strap, a flexible cuff, a belt, a strip, or a Velcro. Accordingly, the first flexible member 1015 and the second flexible member 1017 may be the flexible part of the combined rigid and flexible securing arrangement. According to various embodiments, the first flexible member 1015 may connect the second end 1012*b* of the first curved-bracket 1012 to the first end 1012*a* of the second curved-bracket 1013. Further, the second flexible member 1017 may be connected to the first end 1012*a* of the first curved-bracket 1012. According to various embodiments, a clip 1019 may be attached to the second flexible member 1017. The clip 1019 may be configured for detachable connection with the second end 1013*b* of the second curved-bracket 1013. According to various embodiments, the second end 1013*b* of the second curved-bracket 1013 may be configured to receive the clip 1019 of the second flexible member 1017. According to various embodiments, the clip 1019 may include an interlocking element 1019*a* and the second end 1013*b* of the second curved-bracket 1013 may include a corresponding interlocking element 1019*b*. For example, the interlocking element 1019*a* of the clip 1019 may include spring-loaded ball or spring-loaded plunger, while the corresponding interlocking element 1019*b* of the second curved-bracket 1013 may include a hole or an indentation.

According to various embodiments, the first end 1013*a* of the second curved-bracket 1013 may include a single loop element 1013*c*, for example in the form of a single loop slider. According to various embodiments, the first flexible member 1015 may be connected to the second curved-bracket 1013 by inserting or looping through the single loop element 1013*c*. In this manner, a distance between the second end 1012*b* of the first curved-bracket 1012 and the first end 1012*a* of the second curved-bracket 1013 may be adjusted by adjusting a length of the first flexible member 1015 being inserted or looped through the single loop element 1013*c*. According to various embodiments, the single loop element 1013*c* may also be replaced by a tri-glide buckle element.

According to various embodiments, the clip 1019 may also include a single loop element 1019*c*. According to various embodiments, the second flexible member 1017 may be connected to the clip 1019 by inserting or looping through the single loop element 1019*c*. In this manner, a distance between the first end 1012*a* of the first curved-bracket 1012 and the clip 1019 may be adjusted by adjusting a length of the second flexible member 1017 being inserted or looped through the single loop element 1019*c*. According to various embodiments, the single loop element 1019*c* may also be replaced by a tri-glide buckle element.

According to various embodiments, an end 1015*a* of the first flexible member 1015 may be slidably inserted into the first curved-bracket 1012 in a telescopic manner through the second end 1012*b* of the first curved-bracket 1012. According to various embodiments, an end 1017*a* of the second flexible member 1017 may be slidably inserted into the first curved-bracket 1012 in a telescopic manner through the first end 1012*a* of the first curved-bracket 1012.

According to various embodiments, the first curved-bracket 1012 may include an adjuster element 1011. The end 1015*a* of the first flexible member 1015 may be connected to the adjuster element 1011 and the end 1017*a* of the second flexible member 1017 may be connected to the adjuster element 1011. According to various embodiments, the adjuster element 1011 may be configured to pull the end 1015*a* of the first flexible member 1015 and the end 1017*a* of the second flexible member 1017 towards each other so as to shorten a distance between the two ends 1015*a*, 1017*a* along the first curved-bracket 1012. According to various embodiments, the adjuster element 1011 may include a knob 1011*a* such that turning the knob 1011*a* in a first direction may pull the two ends 1015*a*, 1017*a* towards each other, which turning the knob 1011*a* in a second direction, opposite the first direction, may allow the two ends 1015*a*, 1017*a* to be pulled apart from each other. According to various embodiments, the adjuster element 1011 may be used for fine-adjustment or tightening after the first flexible member 1015 and the second flexible member 1017 have been adjusted via the single loop elements 1013*c*, 1019*c* of the second curved-bracket 1013 and the clip 1019 respectively.

According to various embodiments, the first curved-bracket 1012 may be coupled to the at least one spring module 130, 230 or the linkage assembly 240, 940, while the second curved-bracket 1013 may be coupled to another spring module 130, 230, or another linkage assembly 240, 940. Accordingly, in this configuration, the first flexible member 1015 and the second flexible member 1017 may be adjusted accordingly so as to allow customisable fitting of the attachment part 1010 to the body. According to various embodiments, the attachment part 1010 may include a three-point adjustment arrangement to fit the attachment part 1010 to the body. According to various embodiments, the three-point adjustment arrangement may include the loop element 1013*c* of the second curved-bracket 1013, the loop element 1019*c* of the clip 1019, and the adjuster element 1011 of the first curved-bracket 1012 as shown in FIG. 10. According to various embodiments, the three-point adjustment arrangement of the attachment part 1010 may facilitate the at least one spring module 130, 230, and/or the linkage assembly 240, 940 to always remain at two opposite sides of the body, for example two opposite longitudinal sides of a leg or an arm. Further, the three-point adjustment arrangement of the attachment part 1010 may allow customisable fit which may enhance comfort and support.

Figure 11A:
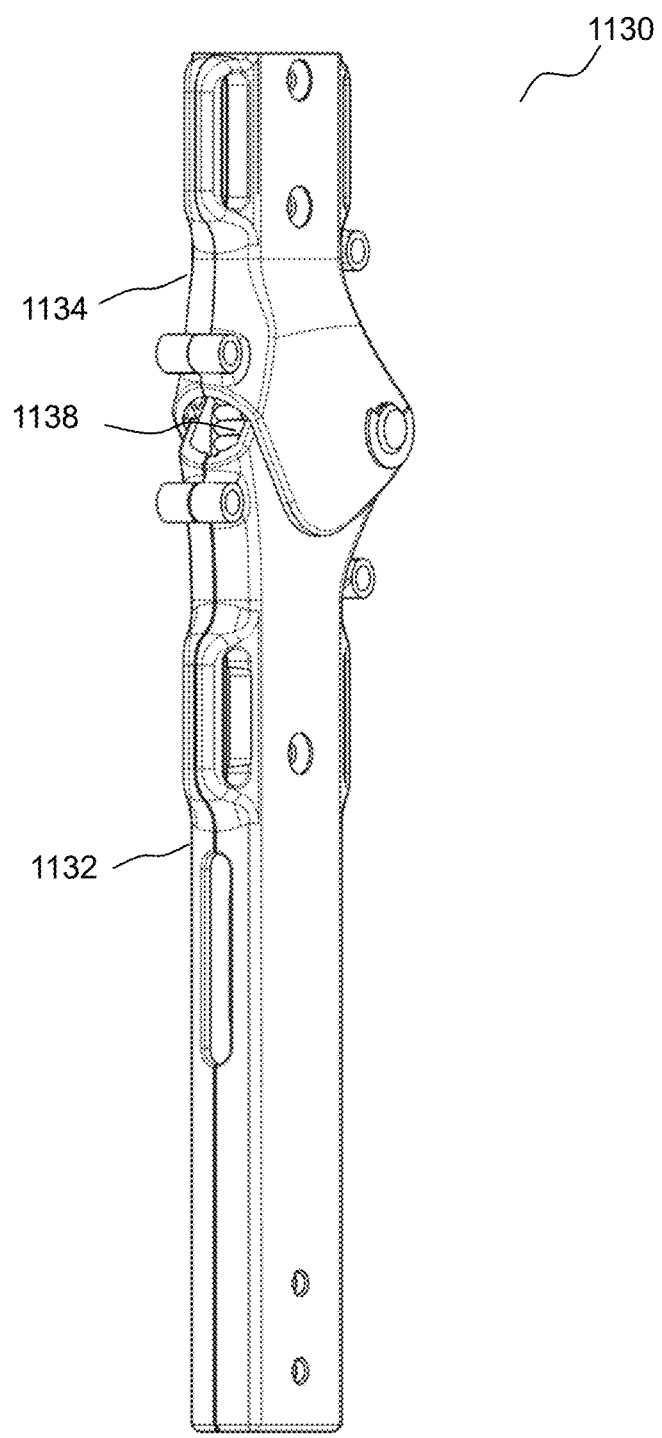
FIG. 11A shows a variant of a spring module according to various embodiments.
Figure 11B:
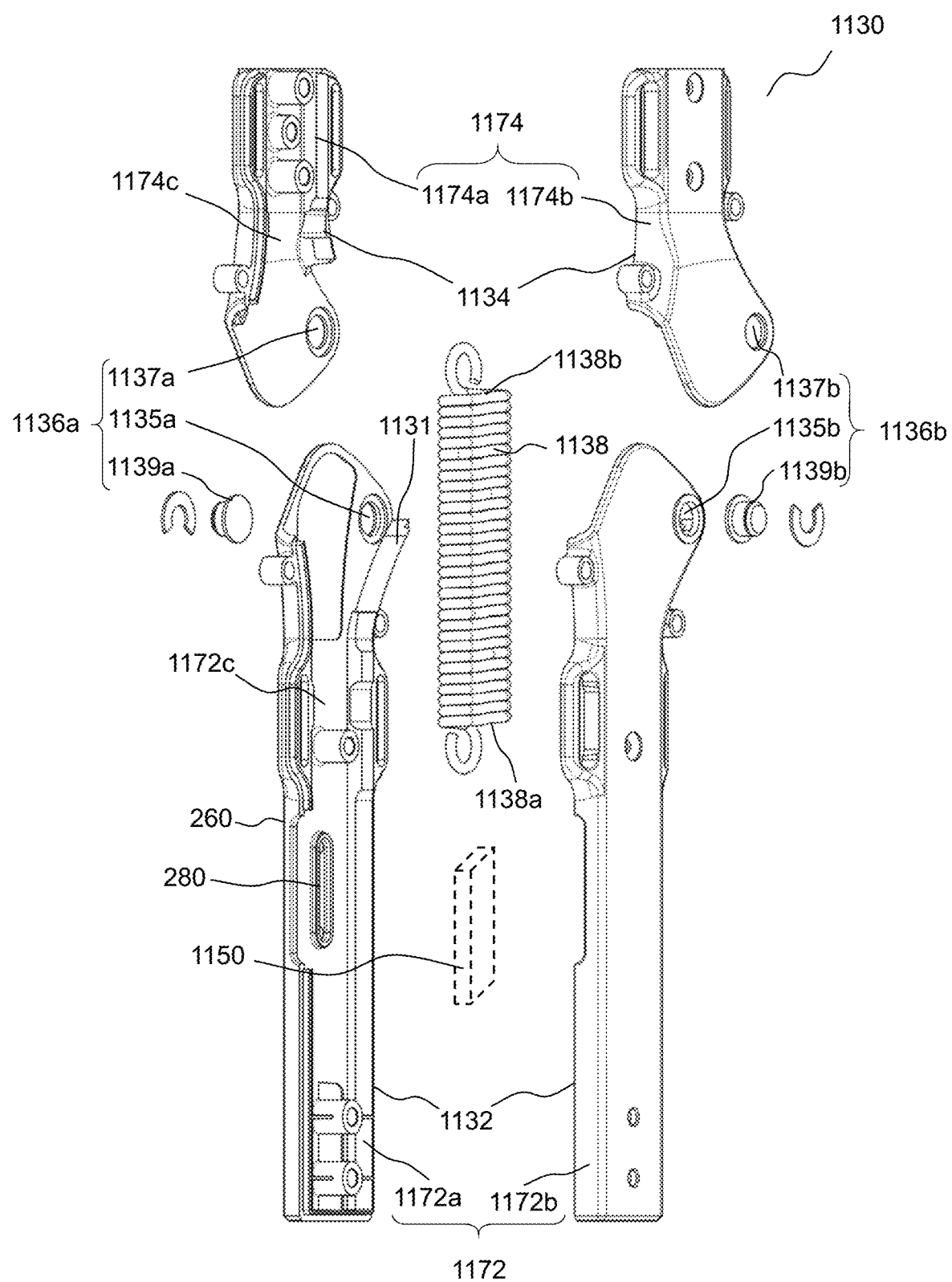
FIG. 11B shows an exploded view of the spring module of FIG. 11A according to various embodiments.

FIG. 11A shows a variant of a spring module 1130 according to various embodiments. FIG. 11B shows an exploded view of the spring module 1130 according to various embodiments. FIG. 12A and FIG. 12B show longitudinal cross-sectional views of the spring module 1130 of FIG. 11A in the longitudinally aligned disposition (i.e. the spring module 1130 being straightened) according to various embodiments. FIG. 13A and FIG. 13B show cross-sectional views of the spring module 1130 of FIG. 11A with first and second elongate link members 1132, 1134 pivoted relative to each other (i.e. the spring module being bent) according to various embodiments. According to various embodiments, the spring module 1130 may be interchangeable with the spring module 230 of the device 200, or the spring module 930 of the device 900. According to various embodiments, the spring module 1130 may also be combined with first attachment part 210 and the second attachment part 220 of the device 200, or the first attachment part 910 and the second attachment part 920 of the device 900, or the attachment part 1010 to form a device for providing active assistance to a body joint between a first portion and a second portion of a body.

According to various embodiments, the spring module 1130 may, similar to the spring module 230 of the device 200 or the spring module 930 of the device 900, include the first elongate link member 1132 and the second elongate link member 1134. According to various embodiments, the first elongate link member 1132 and the second elongate link member 1134 may be pivotably coupled to each other via a pair of coaxial pivot joints 1136a, 1136b (i.e. a first pivot joint 1136a and a second pivot joint 1136b) with a common pivoting axis perpendicular to the first and second elongate link members 1132, 1134. According to various embodiments, a longitudinal end portion of the first elongate link member 1132 and a longitudinal end portion of the second elongate link member 1134 may be pivotably coupled to each other via the pair of pivot joints 1136a, 1136b. According to various embodiments, each pivot joint 1136a, 1136b may be a pin joint or a hinge joint or a revolute joint.

According to various embodiments, the first elongate link member 1132 may include a hollow frame 1172 (or hollow structure). According to various embodiments, the hollow frame 1172 of the first elongate link member 1132 may be formed by two elongate shell parts 1172a, 1172b joined together lengthwise. According to various embodiments, the two elongate shell parts 1172a, 1172b may correspond to the hollow frame 1172 of the first elongate link member 1132 being divided and separated longitudinally. According to various embodiments, the two elongate shell parts 1172a, 1172b may be joined together via screw, bolt and nut, clamp, clip, latch, hook, pin, or any other suitable fastener.

According to various embodiments, the second elongate link member 1134 may include a hollow frame 1174 (or hollow structure). According to various embodiments, the hollow frame 1174 of the second elongate link member 1134 may be formed by two elongate shell parts 1174a, 1174b joined together lengthwise. According to various embodiments, the two elongate shell parts 1174a, 1174b may correspond to the hollow frame 1174 of the second elongate link member 1134 being divided and separated longitudinally. According to various embodiments, the two elongate shell parts 1174a, 1174b may be joined together via screw, bolt and nut, clamp, clip, latch, hook, pin, or any other suitable fastener.

According to various embodiment, the longitudinal end portion of the first elongate link member 1132 may include a first hole 1135a at the first elongate shell part 1172a and a second hole 1135b at the second elongate shell part 1172b. According to various embodiments, the first hole 1135a at the first elongate shell part 1172a and the second hole 1135b at the second elongate shell part 1172b may be coaxial when the first elongate shell part 1172a and the second elongate shell part 1172b are coupled together to form the hollow frame 1172 of the first elongate link member 1132. According to various embodiments, the longitudinal end portion of the second elongate link member 1134 may include a first hole 1137a at the first elongate shell part 1174a and a second hole 1137b at the second elongate shell part 1174b. According to various embodiments, the first hole 1137a at the first elongate shell part 1174a and the second hole 1137b at the second elongate shell part 1174b may be coaxial when the first elongate shell part 1174a and the second elongate shell part 1174b are coupled together to form the hollow frame 1174 of the second elongate link member 1134. According to various embodiments, the first hole 1135a at the longitudinal end portion of the first elongate shell part 1172a of the first elongate link member 1132 may be coupled to the first hole 1137a at the longitudinal end portion of the first elongate shell part 1174a of the second elongate link member 1134 via a first pin 1139a to form the first pivot joint 1136a. According to various embodiments, the second hole 1135b at the longitudinal end portion of the second elongate shell part 1172b of the first elongate link member 1132 may be coupled to the second hole 1137b at the longitudinal end portion of the second elongate shell part 1174b of the second elongate link member 1134 via a second pin 1139b to form the second pivot joint 1136b. According to various embodiments, the first pivot joint 1136a and the second pivot joint 1136b may be coaxial and spaced apart. According to various embodiments, the first elongate link member 1132 and the second elongate link member 1134 may be pivotable relative to each other about the first and second pivot joints 1136a, 1136b such that the first elongate link member 1132 and the second elongate link member 1134 may be moved relative to each other so as to form an angle with respect to each other with respect to the first and second pivot joints 1136a, 1136b.

According to various embodiments, the spring module 1130 may, similar to the spring module 230 of the device 200 or the spring module 930 of the device 900, include a coil spring 1138 extending longitudinally between the first and second elongate link members 1132, 1134 and across the first and second pivot joints 1136a, 1136b. Accordingly, the coil spring 1138 may extend across the common pivoting axis of the first and second pivot joints 1136a, 1136b so as to form a cross configuration with the common pivoting axis of the first and second pivot joints 1136a, 1136b. According to various embodiments, the coil spring 1138 may extend across the first and second pivot joints 1136a, 1136b in a manner so as to be over the common pivoting axis of the first and second pivot joints 1136a, 1136b, or under the common pivoting axis of the first and second pivot joints 1136a, 1136b, or intersecting the common pivoting axis of the first and second pivot joints 1136a, 1136b. According to various embodiments, the coil spring 1138 may intersect the pivoting axis of the first and second pivot joints 1136a, 1136b when the coil spring 1138 extends across and between the first and second pivot joints 1136a, 1136b so as to run transversely across opposing ends of the first and second pivot joints 1136a, 1136b in a manner so as to be abutting or adjacent to respective ends of the first and second pivot joints 1136a, 1136b.

According to various embodiments, the first end 1138a of the coil spring 1138 may be inserted into the first elongate link member 1132 and coupled to an inner wall surface 1172c of the first elongate link member 1132. According to various embodiments, the hollow frame 1172 of the first elongate link member 1132 may include an empty space extending longitudinally along the first elongate link member 1132. According to various embodiments, the first end 1138a of the coil spring 1138 may be inserted into an opening of the hollow frame 1172 of the first elongate link member 1132 at the second longitudinal end portion 1132a of the first elongate link member 1132.

According to various embodiments, the second end 1138b of the coil spring 1138 may be inserted into the second elongate link member 1134 and coupled to an inner wall surface 1174c of the second elongate link member 1134. According to various embodiments, the hollow frame 1174 of the second elongate link member 1134 may include an empty space extending longitudinally along the second elongate link member 1134. According to various embodiments, the second end 1138b of the coil spring 1138 may be inserted into an opening of the hollow frame 1174 of the second elongate link member 1134 at the second longitudinal end portion 1134a of the second elongate link member 1134.

According to various embodiments, the first end 1138a of the coil spring 1138 may be coupled to the first elongate link member 1132 and the second end 1138b of the coil spring 1138 may be coupled to the second elongate link member 1134. According to various embodiments, the coil spring 1138 may be coupled to the first and second elongate link members 1132, 1134 respectively via welding, rivet, or hook. As shown, the spring module 1130 may include one coil spring 1138 extending longitudinally between the first and second elongate link members 1132, 1134 and across the first and second pivot joints 1136a, 1136b.

According to various embodiments, the coil spring 1138 may be arranged and disposed with respect to the first and second elongate link member 1132, 1134 in a manner such that a longitudinal axis of the coil spring 1138 may extend from the first elongate link member 1132 to the second elongate link member 1134, whereby a first end segment of the coil spring 1138 towards the first end 1138a may be parallel to the first elongate link member 1132 and a second end segment of the coil spring 1138 towards the second end 1138b may be parallel to the second elongate link member 1134. According to various embodiments, a direction of a length of the coil spring 1138 may be extending between the first and second elongate link members 1132, 1134 such that the coil spring 1138 runs lengthwise from the first elongate link member 1132 to the second elongate link member 1134. According to various embodiments, the coil spring 1128 may extend or run between the first and second elongate link members 1132, 1134 with the first end segment of the coil spring 1138 running alongside at least a portion of a length of the first elongate link member 1132, a mid-segment of the coil spring 1138 running across the first and second pivot joints 1136a, 1136b (e.g. over first and second pivot joints 1136a, 1136b when straighten as shown in FIG. 12A and FIG. 12B, and intersecting the common pivoting axis of the first and second pivot joints 1136a, 1136b when bent as shown in FIG. 13A and FIG. 13B), and a second end segment of the coil spring 1138 running alongside at least a portion of a length of the second elongate link member 1134. According to various embodiments, when the first elongate link member 1132 and the second elongate link member 1134 forms an angle of 180° with respect to each other at the first and second pivot joints 1136a, 1136b, the coil spring 1138 may be parallel to the first and second elongate link member 1132, 1134. Accordingly, the coil spring 1138 may be aligned to the first and second elongate link member 1132, 1134 such that the first end segment of the coil spring 1138 may be overlapping or side-by-side or alongside or coincide with at least a portion of a length of the first elongate link member 1132, the second end segment of the coil spring 1138 may be overlapping or side-by-side or alongside or coincide with at least a portion of a length of the second elongate link member 1134, and the mid-segment of the coil spring 1138 may extend across the first and second pivot joints 1136a, 1136b.

As shown in FIG. 11B, according to various embodiments, the first and second ends 1138a, 1138b of the coil spring 1138 may be coupled to the first and second elongate link members 1132, 1134 respectively via hook. Accordingly, the first and second ends 1138a, 1138b of the coil spring 1138 may remain stationary or may not be movable relative to the first and second elongate link members 1132, 1134 respectively, and may also be capable of being detached from each other. Hence, the first and second ends 1138a, 1138b of the coil spring 1138 may be removably coupled to the first and second elongate link members 1132, 1134 respectively.

According to various embodiments, as shown in FIG. 12A and FIG. 12B, and FIG. 13A and FIG. 13B, the spring module 1130 may, similar to the spring module 230 of the device 200 or the spring module 930 of the device 900, include a slidable coil-spring-retaining-member 1150 at the first elongate link member 1132. According to various embodiments, the slidable coil-spring-retaining-member 1150 may be disposed at or fitted to the first elongate link member 1132. According to various embodiments, the coil-spring-retaining-member 1150 may be slidable longitudinally relative to the first elongate link member 1132. Accordingly, the coil-spring-retaining-member 1150 may be slidable along a length of the first elongate link member 1132. According to various embodiments, with the first end 1138a of the coil spring 1138 coupled to the first elongate link member 1132, the coil-spring-retaining-member 1150 may be slidable along the first elongate link member 1132 to engage and retain a portion of the length of the coil spring 1138 from the first end 1138a of the coil spring 1138. Accordingly, the portion of the length of the coil spring 1138, from the first end 1138a of the coil spring 1138 towards the second end 1138b, that is engaged and retained by the coil-spring-retaining-member 1150 may be varied by sliding the coil-spring-retaining-member 1150 relative to the first elongate link member 1132. According to various embodiments, with the coil-spring-retaining-member 1150 in engagement and retaining the portion of the length of the coil spring 1138, said portion of the length of the coil spring 1138 may not be subjected or exposed to the pivoting motion between the first and second elongate link members 1132, 1134. Accordingly, the portion of the length of the coil spring 1138 may be constrained or may not be effective in acting against the first relative pivoting motion between the first and second elongate link members 1132, 1134 from the longitudinally aligned disposition of the first and second elongate link members 1132, 1134, and/or augmenting the second relative pivoting motion between the first and second elongate link member 1132, 1134 to return to the longitudinally aligned disposition. According to various embodiments, the portion of the length of the coil spring 1138 engaged and retained by the coil-spring-retaining-member 1150 may correspondingly reduce an effective length of the coil spring 1138 (or an effective number of coils of the coil spring 1138) subjected or exposed to the pivoting motion between the first and second elongate link members 1132, 1134.

According to various embodiments, the coil spring 1138 may have a higher effective lateral stiffness when the effective length of the coil spring 1138 is shorter. Accordingly, by sliding the coil-spring-retaining-member 1150 along the first elongate link member 1132 to engage and retain a portion of the length of the coil spring 1138 from the first end 1138a of the coil spring 1138, the effective length of the coil spring 1138 may be reduced and, thus, the effective lateral stiffness of the coil spring 1138 may be higher. With a higher effective lateral stiffness, the coil spring 1138 may provide a greater force or torque to act against the first relative pivoting motion between the first and second elongate link members 1132, 1134 from the longitudinally aligned disposition of the first and second elongate link members 1132, 1134, and/or to augment the second relative pivoting motion between the first and second elongate link member 1132, 1134 to return to the longitudinally aligned disposition. According to various embodiments, the force or torque provided by the spring module 1130 may be varied by sliding the coil-spring-retaining-member 1150 relative to the first elongate link member 1132 to vary the portion of the length of the coil spring 1138, from the first end 1138a of the coil spring 1138 towards the second end 1138b, engaged and retained by the coil-spring-retaining-member 1150.

According to various embodiments, the coil-spring-retaining-member 1150 may, similar to the coil-spring-retaining-member 250 of device 200, be in the form of a coil-spring-retaining-insert slidable relative to the first elongate link member 1132. According to various embodiments, a free end of the coil-spring-retaining-insert may be slidably inserted into the coil spring 1138 from the first end 1138a thereof. According to various embodiments, by sliding the coil-spring-retaining-insert relative to the first elongate link member 1132, a length of the coil-spring-retaining-insert, from the free end of the coil-spring-retaining-insert towards an opposite end, that is inserted within the coil spring 1138 may be varied. According to various embodiments, by varying the length of the coil-spring-retaining-insert slidably inserted within the coil spring 1138, the portion of the length of the coil spring 1138 engaged and retained by the coil-spring-retaining-insert may by varied so as to vary the effective length of the coil spring 1138 (or an effective number of coils of the coil spring 1138) subjected or exposed to the pivoting motion between the first and second elongate link members 1132, 1134.

According to various embodiments, the coil-spring-retaining-member 1150 may, similar to the coil-spring-retaining-member 950 of device 900, be in the form of a coil-spring-retaining-bracket slidable relative to the first elongate link member 1132. According to various embodiments, the coil-spring-retaining-bracket may slide over the coil spring 1138 from the first end 1138a thereof for engaging and retaining a portion of a length of the coil spring 1138. According to various embodiments, by sliding the coil-spring-retaining-bracket relative to the first elongate link member 1132, the coil-spring-retaining-bracket may slide over a portion of a length of the coil spring 1138, from the first end 1138a of the coil spring 1138 towards a second end 1138b. According to various embodiments, by varying the portion of the length of the coil spring 1138 engaged and retained by the coil-spring-retaining-bracket, an effective length of the coil spring 1138 (or an effective number of coils of the coil spring 1138), which is subjected or exposed to the pivoting motion between the first and second elongate link members 1132, 1134, may be varied.

According to various embodiments, the spring module 1130 may, similar to the spring module 230 of the device 200, include a locking mechanism to lock the slidable coil-spring-retaining-member 1150 to the first elongate link member 1132. According to various embodiments, the locking mechanism may be any suitable locking mechanism, for example, a spring-loaded ball type locking mechanism whereby the first elongate link member 1132 includes a series of holes or indentations along its length and the slidable coil-spring-retaining-member 1150 include a spring-loaded ball to engage with the holes or indentations; or a spring-loaded plunger type locking mechanism whereby the first elongate link member 1132 includes a series of holes or indentations along its length and the slidable coil-spring-retaining-member 1150 include a spring-loaded ball to engage with the holes or indentations; or a ratchet type locking mechanism whereby the first elongate link member 1132 includes a series of teeth along its length and the slidable coil-spring-retaining-member 1150 include a spring-loaded pawl to engage with the teeth.

According to various embodiments, the first elongate link member 1132 may include a bending support 1131 at the longitudinal end portion of the first elongate link member 1132. According to various embodiments, the bending support 1131 may be extending diagonally with respect to the first elongate link member 1132. According to various embodiments, the bending support 1131 may be adjacent to the first and second pivot joints 1136a, 1136b. According to various embodiments, when the spring module 1130 is straighten, the mid-segment of the coil spring 1138 may be at the forward side of the first and second pivot joints 1136a, 1136b and the bending support 1131 may be at the rearward side of the first and second pivot joints 1136a, 1136b. According to various embodiments, when the spring module 1130 is bent, the bending support 1131 may prop or hold up the mid-segment of the coil spring 1138 for bending the coil spring 1138 during pivoting motion of the first and second elongate link members 1132, 1134 about the pivot joints 1136. Accordingly, during bending of the spring module 1130, the mid-segment of the coil spring 1138 may slide between the first and second pivot joints 1136a, 1136b so as to rest on the bending support 1131 such that the bending support 1131 may prop or hold up the mid-segment of the coil spring 1138 to bend the coil spring 1138 as the first and second elongate link members 1132, 1134 pivot about the first and second pivot joints 1136a, 1136b.

According to various embodiments, the first elongate link member 1132 may include a longitudinal slot 1180 along a wall portion of the hollow frame 1172 of the first elongate link member 1132. According to various embodiments, the longitudinal slot 1180 may be extending lengthwise along the wall portion of one of the two elongate shell parts 1172a, 1172b of the hollow frame 1172 of the first elongate link member 1132. According to various embodiments, the coil-spring-retaining-member 1150 may include a protrusion extending perpendicularly from the coil-spring-retaining-member 1150 and through the longitudinal slot 1180. According to various embodiments, the protrusion of the coil-spring-retaining-member 250 may penetrates the wall portion of one of the two elongate shell parts 1172a, 1172b of the hollow frame 1172 of the first elongate link member 1132 through the longitudinal slot 1180. Accordingly, the protrusion of the coil-spring-retaining-member 1150 may be slidden along the longitudinal slot 1180 for controlling the relatively sliding movement of the coil-spring-retaining-member 1150 with respect to the hollow frame 1172 of the first elongate link member 1132 for varying the effective length of the coil spring 1138.

Various embodiments have provided a device for providing active assistance to a body joint which is simple and effective. According to various embodiments, the device may provide a force or torque against a pivoting motion of a joint and/or augment a pivoting motion of the joint in a simple and efficient manner.

While the invention has been particularly shown and described with reference to specific embodiments, it should be understood by those skilled in the art that various changes, modification, variation in form and detail may be made therein without departing from the scope of the invention as defined by the appended claims. The scope of the invention is thus indicated by the appended claims and all changes which come within the meaning and range of equivalency of the claims are therefore intended to be embraced.

The invention claimed is:

1. A device for providing active assistance to a body joint between a first portion and a second portion of a body, the device comprising:
    a first attachment part configured to hold the device to the first portion of the body;
    a second attachment part configured to hold the device to the second portion of the body; and
    at least one spring module interconnecting the first attachment part and the second attachment part, the at least one spring module comprises a first elongate link member coupled to the first attachment part;
a second elongate link member coupled to the second attachment part, wherein the first elongate link member and the second elongate link member are pivotably coupled to each other at a pivot joint with a pivoting axis perpendicular to the first and second elongate link members; and
a coil spring extending longitudinally between the first and second elongate link members and across the pivot joint, wherein a first end of the coil spring is coupled to the first elongate link member and a second end of the coil spring is coupled to the second elongate link member, wherein a mid-segment of the coil spring is adjacent the pivot joint and the coil spring bends when the first elongate link member and the second elongate member are pivoted relative to each other about the pivot joint to form an angle with respect to each other;
wherein the at least one spring module further comprises a slidable coil-spring-retaining-member at the first elongate link member, the coil-spring-retaining-member being slidable relative to the first elongate link member in a manner so as to vary a portion of a length of the coil spring, from the first end of the coil spring towards the second end, engaged and retained by the coil-spring-retaining-member to vary an effective length of the coil spring, the effective length of the coil spring being a remaining portion of the length of the coil spring unconstrained by the coil-spring-retaining-member and available for bending as the first elongate link member and the second elongate member pivot relative to each other about the pivot joint;
wherein the coil-spring-retaining-member comprises a coil-spring-retaining-insert slid able relative to the first elongate link member in a manner so as to vary a length of the coil-spring-retaining-insert, from a free end of the coil-spring-retaining-insert towards an opposite end, slidably inserted within the coil spring from the first end thereof to vary the portion of the length of the coil spring engaged and retained by the coil-spring-retaining-insert to vary the effective length of the coil spring;
wherein the first elongate link member comprises a hollow frame, wherein the first end of the coil spring is inserted into the first elongate link member and coupled to an inner wall surface of the first elongate link member, and wherein the second elongate link member comprises a hollow frame, wherein the second end of the coil spring is inserted into the second elongate link member and coupled to an inner wall surface of the second elongate link member;
wherein a coil-spring-retaining-insert is slidable inside the hollow frame of the first elongate link member, wherein the first elongate link member comprises a longitudinal slot along a wall portion of the hollow frame, and wherein the coil-spring-retaining-insert comprises a protrusion extending from the coil-spring-retaining-insert and through the longitudinal slot.

2. The device as claimed in claim 1, wherein the coil spring of the at least one spring module is configured to provide a torque, based on a lateral stiffness of the coil spring, against a relative pivoting motion about the pivot joint between the first and second elongate link members from a longitudinally aligned disposition of the first and second elongate link members.

3. The device as claimed in claim 1, wherein the coil spring comprises a rectangular-shaped coil spring, a pill-shaped coil spring, or a wedged-shape coil spring.

4. The device as claimed in claim 1, wherein the coil-spring-retaining-member comprises a coil-spring-retaining-bracket slidable relative to the first elongate link member in a manner so as to vary the length of the coil spring, from the first end of the coil spring towards the second end, engaged and retained within the coil-spring-retaining-bracket to vary the effective length of the coil spring.

5. The device as claimed in claim 1, wherein the at least one spring module further comprises a locking mechanism to lock the slidable coil-spring-retaining-member to the first elongate link member.

6. The device as claimed in claim 1,
wherein a longitudinal end portion of the first elongate link member comprises a diagonal arm extending therefrom,
wherein a longitudinal end portion of the second elongate link member comprises a diagonal arm extending therefrom,
wherein a tip portion of the diagonal arm of the first elongate link member is pivotably coupled to a tip portion of the diagonal arm of the second elongate link member in a manner so as to form the pivot joint immediately adjacent to the mid-segment of the coil spring when the coil spring is aligned with the first and second elongate link members.

7. The device as claimed in claim 1, wherein each of the first attachment part and the second attachment part comprises a curved-bracket having a curvature extending from a first end to a second end, the curvature of the curved-bracket being shaped to correspond to a transverse contour of the first portion and the second portion of the body respectively.

8. The device as claimed in claim 7,
wherein the at least one spring module interconnects the first end of the curved-bracket of the first attachment part and the first end of the curved-bracket of the second attachment part,
wherein the first elongate link member is coupled directly to the first end of the curved-bracket of the first attachment part,
wherein the second elongate link member is coupled directly to the first end of the curved-bracket of the second attachment part, and
wherein the device is free of other components interconnecting the first end of the curved-bracket of the first attachment part and the first end of the curved-bracket of the second attachment part.

9. The device as claimed in claim 8, further comprising a linkage assembly interconnecting the second end of the curved-bracket of the first attachment part and the second end of the curved-bracket of the second attachment part, the linkage assembly comprises
a first link rod coupled to the second end of the curved-bracket of the first attachment part; and
a second link rod coupled to the second end of the curved-bracket of the second attachment part,
wherein the first link rod and the second link rod are pivotably coupled to each other at a pivot joint which is coaxial with the pivot joint between the first and second elongate link members of the at least one spring module.

10. The device as claimed in claim 7, wherein the device comprises a first spring module interconnecting the first end of the curved-bracket of the first attachment part and the first end of the curved-bracket of the second attachment part, and a second spring module interconnecting the second end of the curved-bracket of the first attachment part and the second end of the curved-bracket of the second attachment part.

11. The device as claimed in claim 10, wherein the device is free of other components interconnecting the first attachment part and the second attachment part.

12. The device as claimed in claim 1, wherein the at least one spring module is removably coupled to the first attachment part and the second attachment part.

13. The device as claimed in claim 1, wherein the first elongate link member and the second elongate link member are pivotably coupled to each other via a pair of coaxial pivot joints with a common pivoting axis perpendicular to the first and second elongate link members.

14. The device as claimed in claim 13,
wherein the first elongate link member comprises a hollow frame, wherein the first end of the coil spring is inserted into the first elongate link member and coupled to an inner wall surface of the first elongate link member, and wherein the second elongate link member comprises a hollow frame, wherein the second end of the coil spring is inserted into the second elongate link member and coupled to an inner wall surface of the second elongate link member.

15. The device as claimed in claim 14,
wherein the first elongate link member comprises a first hole and a second hole at an longitudinal end portion thereof, wherein the second elongate link member comprises a first hole and a second hole at an longitudinal end portion thereof, wherein the first hole of the first elongate link member is coupled to the first hole of the second elongate link member via a first pin to form a first pivot joint of the pair of coaxial pivot joints, and the second hole of the first elongate link member is coupled to the second hole of the second elongate link member via a second pin to form a second pivot joint of the pair of coaxial pivot joints.

16. The device as claimed in claim 15, wherein the first elongate link member comprises a bending support extending diagonally at the longitudinal end portion of the first elongate link member.

* * * * *